United States Patent [19]
Demuth, Jr. et al.

[11] Patent Number: 5,387,748
[45] Date of Patent: Feb. 7, 1995

[54] ANTIMICROBIAL DITHIOCARBAMOYL QUINOLONES

[75] Inventors: Thomas P. Demuth, Jr., Norwich; Ronald E. White, South Plymouth, both of N.Y.

[73] Assignee: Procter & Gamble Pharmaceuticals, Inc., Norwich, N.Y.

[21] Appl. No.: 696,985

[22] Filed: May 2, 1991

Related U.S. Application Data

[63] Continuation of Ser. No. 418,029, Oct. 12, 1989, abandoned, which is a continuation-in-part of Ser. No. 261,948, Oct. 24, 1988, abandoned.

[51] Int. Cl.$^6$ .................. C07D 501/20; A61K 31/495
[52] U.S. Cl. ..................................... 514/254; 514/312; 544/363; 546/156
[58] Field of Search .................. 540/222; 544/363; 514/312, 254; 546/156

[56] References Cited

U.S. PATENT DOCUMENTS

| | | | |
|---|---|---|---|
| 4,146,719 | 3/1979 | Irikura | 544/363 |
| 4,620,007 | 10/1986 | Grohe et al. | 546/156 |
| 4,631,150 | 12/1986 | Battistini et al. | 540/310 |
| 4,670,444 | 6/1987 | Grohe et al. | 514/300 |
| 4,742,053 | 5/1988 | Nakagawa et al. | 514/202 |
| 4,806,541 | 2/1989 | Joliden et al. | 544/363 |
| 4,874,764 | 10/1989 | Weda et al. | 544/363 |
| 4,904,647 | 2/1990 | Kulcsar et al. | 514/154 |
| 4,954,507 | 9/1990 | Weber et al. | 544/263 |
| 5,013,730 | 5/1991 | Arnould et al. | 514/202 |
| 5,013,731 | 5/1991 | Arnould et al. | 514/202 |
| 5,328,908 | 7/1994 | Damuth et al. | 544/363 |

FOREIGN PATENT DOCUMENTS

| | | |
|---|---|---|
| 8775009 | 1/1988 | Australia . |
| 8827554 | 6/1989 | Australia . |
| 53816 | 6/1982 | European Pat. Off. . |
| 62328 | 10/1982 | European Pat. Off. . |
| 203559 | 12/1986 | European Pat. Off. . |
| 0304158 | 2/1989 | European Pat. Off. . |
| 335297 | 10/1989 | European Pat. Off. . |
| 341990 | 11/1989 | European Pat. Off. . |
| 0366189 | 5/1990 | European Pat. Off. . |
| 0366193 | 5/1990 | European Pat. Off. . |
| 0366640 | 5/1990 | European Pat. Off. . |
| 0366641 | 5/1990 | European Pat. Off. . |
| 0451764 | 10/1991 | European Pat. Off. . |
| 0453924 | 10/1991 | European Pat. Off. . |
| 0453952 | 10/1991 | European Pat. Off. . |
| 2191556 | 3/1974 | France . |
| 2243940 | 4/1975 | France . |
| 1940511 | 3/1970 | Germany . |
| 2322750 | 11/1972 | Germany . |
| 2448966 | 4/1975 | Germany . |
| 2514322 | 10/1975 | Germany . |
| 2947948 | 6/1980 | Germany . |
| 3345093 | 6/1984 | Germany . |
| 47-11237 | 4/1972 | Japan . |
| 49-35392 | 4/1974 | Japan . |
| 50-23036 | 8/1975 | Japan . |
| 50-23037 | 8/1975 | Japan . |
| 57-32290 | 2/1982 | Japan . |
| 57-46988 | 3/1982 | Japan . |
| 57-46990 | 3/1982 | Japan . |
| 60-6617 | 1/1985 | Japan . |
| 1258684 | 10/1989 | Japan . |
| 8705297 | 9/1987 | WIPO . |
| WO911631 | 10/1991 | WIPO . |
| WO9116327 | 10/1991 | WIPO . |

OTHER PUBLICATIONS

Georgopapadakou et al., "Mode of Action of the Dual-Action Cephalosporin Ro 23-9424", 33 *Antimicrobial Agents and Chemotherapy* 1067 (1989).

Cleeland et al., "Dual-Action Antibacterials: A Concept Newly Recognized for Antibacterial Chemotherapy", 6 *Antimicrobic Newsletter* 61 (1989).

Albrecht et al., "Dual-Action Cephalosporins: Cethalosporin-3'-Quaternary Quinolones", *Program and Abstracts of the Twenty-Ninth Interscience Conference on Antimicrobial Agents and Chemotherapy* (American Society for *Microbiology*, 1989).

Uglesic et al., "New Semisynthetic Penicillins", *Advan. Antimicrob. Antineoplastic Chemother., Proc. Int. Congr. Chemother., 7th*, Meeting Date 1971, vol. 1, 997 (1972) (*Chemical Abstracts* 79:61968).

O'Callaghan, et al., "A New Cephalosporin with a Dual Mode of Action", 10 *Antimicrobial Agents and Chemotherapy* 245 (1976).

Greenwood et al., "Dual-Action Cephalosporin Utilizing a Novel Therapeutic Principle", 10 *Antimicrobial Agents and Chemotherapy* 249 (1976).

Yamada et al., "New Broad-Spectrum Cephalosporins with Antipseudomonal Activity", 36 *J. Antibiotics* 532 (1983) (*Chemical Abstracts* 99:87869).

Hirose et al., "Desulfurization of 7-Aminodeacetoxycephalosporanic Acid", 104 *Yakugaku Zasshi* 302 (1984) (*Chemical Abstract* 101:110596).

Cimarusti et al., "Monocyclic β-Lactam Antibiotics", 4 *Medicinal Research Reviews* 1 (1984).

Dürckheimer et al., "Recent Developments in the Field of β-Lactam Antibiotics", 24 *Angew. Chem. Int. Ed. Engl.* 180 (1985).

Wolfson et al., "Minireview—The Fluoroquinolones: Structures, Mechanisms of Action and Resistance, and Spectra of Activity In Vitro", 28 *Antimicrobial Agents and Chemotherapy* 581 (1985).

Mobashery et al., "Conscripting β-Lactamase for Use in Drug Delivery. Synthesis and Biological Activity of a Cephalosporin $C_{10}$-Ester of an Antibiotic Dipeptide", 108 *J. American Chemical Society* 1685 (1986).

Mobashery et al., "Reactions of *Escherichia coli* TEM β-Lactamase with Cephalothin and with $C_{10}$-Dipeptidyl Cephalosporin Esters", 261 *J. Biological Chemistry* 7879 (1986).

Rolinson, "β-Lactam antibiotics", 17 *J. Antimicrobial Chemotherapy* 5 (1986).

Wise, "Minireview—In Vitro and Pharmacokinetic Properties of the Carbapenems", 30 *Antimicrobial Agents and Chemotherapy* 343 (1986).

Mobashery et al., "Inactivation of Alanine Racemase by β-Chloro-L-alanine Released Enzymatically from Amino Acid and Peptide $C_{10}$ Esters of Deacetylcephalothin", 26 i Biochemistry 5878 (1987).

Thabaut et al., "Beta-lactam Antibiotic—New Quinolone Combinations", 16 *Presse Med.* 2167 (1987) (*Chemical Abstracts* 108:147028).

Le Noc et al., "Activite Antibacterienne in vitro du Cefpirome en Association Avec Quatre Aminoglycosides et Deux Fluoroquinolones", 36 *Path. Biol.* 762 (1988).

McCombie et al., "Synthesis and In Vitro Activity of the Penem Antibiotics", 8 *Medicinal Research Reviews* 393 (1988).

Albrecht et al., "Dual-Action Cephalosporins: An Idea Whose Time Has Come", *Program and Abstracts of the Twenty-Eighth Interscience Conference on Antimicrobial Agents and Chemotherapy* 186 (American Society for Microbiology, 1988).

Georgopapadakou et al., "Cephalosporin-Quinolone Esters: Biological Properties", *Program and Abstracts of the Twenty-Eighth Interscience Conference on Antimicrobial Agents and Chemotherapy* 186 (American Society for Microbiology, 1988).

Christenson et al., "Hydrolysis of Ro 23-9424 by β-Lactamases", *Program and Abstracts of the Twenty-Eighth Interscience Conference on Antimicrobial Agents and Chemotherapy* 187 (American Society for Microbiology, 1988).

Christenson et al., "Mode of Action of Ro 23-9424, a Dual-Action Cephalosporin", *Program and Abstracts of the Twenth-Eighth Interscience Conference on Antimicrobial Agents and Chemotherapy* 187 (American Society for Microbiology, 1988).

Georgopapadakou et al., "Mode of Action of the Dual-Action Cephalosporin Ro 23-9424", *Program and Abstracts of the Twenty-Eighth Interscience Conference on Antimicrobial Agents and Chemotherapy* 187 (American Society for Microbiology, 1988).

Jones et al., "Antimicrobial Activity of Ro 23-9424, a Novel Ester Fusion of Fleroxacin and Desacetyl-Cefotaxime", *Program and Abstracts of the Twenty-Eighth Interscieence Conference on Antimicrobial Agents and Chemotherapy* 187 (American Society for Microbiology, 1988).

Beskid et al., "In Vitro Antibacterial Activity of Dual-Action Cephalosporin Ro 23-9424 and Comparative Agents", *Program and Abstracts of the Twenty-Eighth Interscience Conference on Antimicrobial Agents and Chemotherapy* 187 (American Society for Microbiology, 1988).

Beskid et al., "In Vivo Antibacterial Activity of Dual-Action Cephalosporin Ro 23-9424 Compared to Cefotaxime and Fleroxacin", *Program and Abstracts of the Twenty-Eighth Interscience Conference on Antimicrobial Agents and Chemotherapy* 187 (American Society for Microbiology, 1988).

Christenson et al., "Pharmacokinetics of Ro 23-9424, a Dual-Action Cephalosporin in Animals", *Program and Abstracts of the Twenty-Eighth Interscience Conference on Antimicrobial Agents and Chemotherapy* 188 (American Society for Microbiology, 1988).

Christenson et al., "Mode of Action of Ro 23-5068, a Dual-Action Cephalosporin", *Program and Abstracts of the Twenty-Eighth Interscience Conference on Antimicrobial Agents and Chemotherapy* 188 (American Society for Microbiology, 1988).

Albrecht et al., "Dual-Action Cephalosporins: An Idea Whose Time Has Come", Poster Session: 28th Interscience Conference on Antimicrobial Agents and Chemotherapy (Oct. 24, 1988).

Georgopapadakou et al., "Cephalosporin-Quinolone Esters: Biological Properties", Poster Session: 28th Interscience Conference on Antimicrobial Agents and Chemotherapy (Oct. 24, 1988).

Christenson et al., "Hydrolysis of Ro 23-9424 by β-Lactamases", Poster Session: 28th Interscience Conference on Antimicrobial Agents and Chemotherapy (Oct. 24, 1988).

Christenson et al., "Mode of Action of Ro 23-9424, a 'Dual-Action' Cephalosporin", Poster Session: 28th Interscience Conference on Antimicrobial Agents and Chemotherapy (Oct. 24, 1988).

Georgopapadakou et al., "Mode of Action of the Dual-Action Cephalosporin Ro 23-9424", Poster Session: 28th Interscience Conference on Antimicrobial Agents and Chemotherapy (Oct. 24, 1988).

Beskid et al., "In Vitro Antibacterial Activity of Dual-Action Cephalosporin Ro 23-9424 and Comparative Agents", Poster Session: 28th Interscience Conference on Antimicrobial Agents and Chemotherapy (Oct. 24, 1988).

Beskid et al., "In Vivo Antibacterial Activity of Dual-Action Cephalosporin Ro 23-9424 Compared to Cefotaxime and Fleroxacin", Poster Session: 28th Interscience Conference on Antimicrobial Agents and Chemotherapy (Oct. 24 1988).

Christenson et al., "Pharmacokinetics of Ro 23-9424, a Dual-Action Cephalosporin, in Animals", Poster Session: 28th Interscience Conference on Antimicrobial Agents and Chemotherapy (Oct. 24, 1988).

Christenson et al., "Mode of Action of Ro 23-5068, a Dual-Action Cephalosporin", Poster Session: 28th Interscience Conference on Antimicrobial Agents and Chemotherapy (Oct. 24, 1988).

Perrone, E. et al., "Dual Action Penems", Abstract #825; *Abstracts of the 1991 ICAAC* (Abstract only).

Albrecht, H. A., "Dual-Action Cephalosporins Incorporating 3'-Tertiary Amine-Linked Quinolones", *31st Interscience Conference on Antibacterial Agents and Chemotherapy*, Chicago, Illinois; Poster Session: Oct. 2, 1991 (Abs. & Poster).

Corraz, A. J. et al., "Dual-Action Penems and Carbapenems", Abstract #826, Poster #73, *31st Interscience Conference on Antimicrobial Agents and Chemotherapy* (Chicago, Illinois), Oct. 1, 1991 (Abstract & Poster).

Schaefer, F. F. et al., "The Role of AMPC β-Lactamase in the Mechanism of Action of Ester-Linked Dual-Action Cephalosporins", Abstract #953, *31st Inter-Science Conference on Antimicrobial Agents and Chemotherapy*, Poster Session, Oct. 1, 1991 (Abstract & Poster).

Bartkovitz, D., et al., "The Synthesis and Biological Properties of 2a-Methyl Substituted Penicillins", Abstract #824, *31st Interscience Conference on Antibacterial Agents and Chemotherapy* (Chicago, Illinois), Oct. 1, 1991 (Abstract & Poster).

Demuth, T. P., et al., "Synthesis and Antibacterial Activity of New C-10 Quinolonyl-Cephem Esters", *The Journal of Antibiotics*, vol. 44, No. 2, pp. 200–209, Feb. 1991.

*Primary Examiner*—Nicholas S. Rizzo
*Attorney, Agent, or Firm*—Carl J. Roof; Karen F. Clark; David L. Suter

[57]     ABSTRACT

Antimicrobial dithiocarbamoyl quinolone compounds of the general formula:

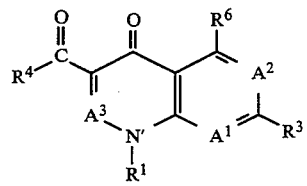

wherein
(1) $A^1$, $A^2$, $A^3$, $R^1$, $R^3$, $R^4$, and $R^6$ form any of a variety of quinolone and related heterocyclic structures similar to those known in the art to have antimicrobial activity; and
(2)

(1) $R^1$ is X, $R^3$ is X, or both $R^1$ and $R^3$ are X; and (2) X is $-R^{15}-N(R^{16})(R^{17})$ or $-R^{15}-R^{18}-N(R^{19})(R^{17})$, where (a)
    (1) $R^{15}$ is nil, alkyl, a carbocyclic ring, or a heterocyclic ring; and
    (2) $R^{16}$ is hydrogen; alkyl; alkenyl; a carbocyclic ring; a heterocyclic ring; or
    (3) when X is $R^{15}-N(R^{16})(R^{17})$, $R^{16}$ and $R^{15}$ may together comprise a heterocyclic ring including the nitrogen atom to which $R^{15}$ and $R^{16}$ are bonded;

(b) $R^{17}$ is $C(=S)-S-M$, where M is a pharmaceutically-acceptable salt or biohydrolyzable ester; and (c)
    (1) $R^{18}$ is alkyl, a carbocyclic ring, or a heterocyclic ring; and
    (2) $R^{19}$ is hydrogen; alkyl; alkenyl; a carbocyclic ring; a heterocyclic ring; or
    (3) $R^{18}$ and $R^{19}$ may together comprise a heterocyclic ring including the nitrogen atom to which $R^{18}$ and $R^{19}$ are bonded;

and pharmaceutically-acceptable salts and biohydrolyzable esters thereof, and hydrates thereof.

35 Claims, No Drawings

ANTIMICROBIAL DITHIOCARBAMOYL QUINOLONES

This is a continuation of application Ser. No. 07/418,029, filed Oct. 12, 1989, now abandoned, which was a continuation-in-part of U.S. patent application Ser. No. 07/261,948, filed Oct. 24, 1988, abandoned.

BACKGROUND OF THE INVENTION

This invention relates to novel antimicrobial compounds and compositions. In particular, the compounds of this invention contain a quinolone or related heterocyclic moiety.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

The mechanism of action of these antibacterials vary. However, each can be generally classified as functioning in one or more of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use, also vary considerably. For example, the classes of antimicrobials (and members within a class) may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The pharmaceutical literature is replete with attempts to develop improved antimicrobials (i.e., compounds that have a broader scope of activity, greater potency, improved pharmacology, and/or less susceptibility to resistance development.) For example, one group of antimicrobials that has been developed relatively recently for clinical use is the quinolones. These compounds include, for example, nalidixic acid, difloxacin, enoxacin, fleroxacin, norfloxacin, lomefloxacin, ofloxacin, ciprofloxacin, and pefloxacin. See, C. Marchbanks and M. Dudley, "New Fluoroquinolones", 7 *Hospital Therapy* 18 (1988); P. Shah, "Quinolones", 31 *Prog. Drug Res.* 243 (1987); *Quinolones—Their Future in Clinical Practice*, (A. Percival, editor, Royal Society of Medical Services, 1986); and M. Parry, "Pharmacology and Clinical Uses of Quinolone Antibiotics", 116 *Medical Times* 39 (1988).

However, many such attempts to produce improved antimicrobials have produced equivocal results. Indeed, few antimicrobials are developed that are truly clinically-acceptable in terms of their spectrum of antimicrobial activity, avoidance of microbial resistance, and pharmacology. For example, the quinolones often show reduced effectiveness against certain clinically important pathogens (for example, gram positive bacteria and/or anaerobic bacteria). The quinolones also have limited water solubility limiting their bioavailability and suitability for parenteral dosing. They may also produce adverse side effects, such as gastrointestinal disturbance and central nervous system effects (such as convulsions). See, M. Neuman and A. Esanu, "Gaps and Perspectives of New Fluoroquinolones", 24 *Drugs Exptl. Clin. Res.* 385 (1988); W. Christ et al., "Specific Toxicologic Aspects of the Quinolones", 10 *Rev. Infectious Diseases* S141 (1988); H. Neu, "Clinical Use of the Quinolones", *Lancet* 1319 (1987); and "Ciprofloxacin: Panacea or Blunder Drug?", *J. South Carolina Med. Assoc* 131 (March 1989).

SUMMARY OF THE INVENTION

The present invention provides compounds of the general structure:

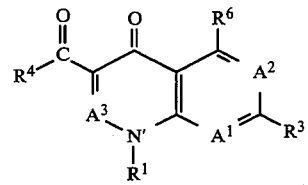

wherein
(A)
(1) $A^1$ is N or $C(R^7)$; where
(i) $R^7$ is hydrogen, hydroxy, alkoxy, nitro, cyano, halogen, alkyl, or $N(R^8)(R^9)$, and
(ii) $R^8$ and $R^9$ are, independently, $R^{8a}$; where $R^{8a}$ is hydrogen, alkyl, alkenyl, carbocyclic ring, or heterocyclic ring substituents; or $R^8$ and $R^9$ together comprise a heterocyclic ring including the nitrogen to which they are bonded;
(2) $A^2$ is N or $C(R^2)$; where $R^2$ is hydrogen or halogen;
(3) $A^3$ is N or $C(R^5)$; where $R^5$ is hydrogen;
(4) $R^1$ is hydrogen, alkyl, a carbocyclic ring, a heterocyclic ring, alkoxy, hydroxy, alkenyl, arylalkyl, $N(R^8)(R^9)$, or X;
(5) $R^3$ is hydrogen, halogen, alkyl, a carbocyclic ring, a heterocyclic ring, or X;
(6) $R^4$ is hydroxy; and
(7) $R^6$ is hydrogen, halogen, nitro or $N(R^8)(R^9)$;
(B) except that
(1) when $A^1$ is $C(R^7)$, $R^1$ and $R^7$ may together comprise a heterocyclic ring including N' and $A^1$;

(2) when $A^2$ is $C(R^2)$, $R^2$ and $R^3$ may together comprise —O—$(CH_2)_n$—O—, where n is from 1 to 4;
(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and
(4) when $A^3$ is $C(R^5)$, $R^1$ and $R^5$ may together comprise a heterocyclic ring including N' and the adjacent carbon to which $R^5$ is bonded;

(C) and
(1) $R^1$ is X, $R^3$ is X, or both $R^1$ and $R^3$ are X; and
(2) X is —$R^{15}$—$N(R^{16})(R^{17})$ or —$R^{15}$—$R^{18}$—$N(R^{19})(R^{17})$, where
(a)
(1) $R^{15}$ is nil, alkyl, a carbocyclic ring, or a heterocyclic ring; and
(2) $R^{16}$ is hydrogen; alkyl; alkenyl; a carbocyclic ring; a heterocyclic ring; or
(3) when X is $R^{15}$—$N(R^{16})(R^{17})$, $R^{16}$ and $R^{15}$ may together comprise a heterocyclic ring including the nitrogen atom to which $R^{15}$ and $R^{16}$ are bonded;
(b) $R^{17}$ is C(=S)—S—M, where M is a pharmaceutically-acceptable salt or biohydrolyzable ester; and
(c)
(1) $R^{18}$ is alkyl, a carbocyclic ring, or a heterocyclic ring; and
(2) $R^{19}$ is hydrogen; alkyl; alkenyl; a carbocyclic ring; a heterocyclic ring; or
(3) $R^{18}$ and $R^{19}$ may together comprise a heterocyclic ring including the nitrogen atom to which $R^{18}$ and $R^{19}$ are bonded;
and pharmaceutically-acceptable salts and biohydrolyzable esters thereof, and hydrates thereof.

It has been found that the compounds of this invention, and compositions containing these compounds, are effective antimicrobial agents against a broad range of pathogenic microorganisms. These compounds provide advantages versus antimicrobial agents among those known in the art, including (for example) the spectrum of antimicrobial activity, potency, and improved pharmacology.

DESCRIPTION OF THE INVENTION

The present invention encompasses certain novel dithiocarbamoyl quinolones, methods for their manufacture, dosage forms, and methods of administering the dithiocarbamoyl quinolones to a human or other animal subject. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

Dithiocarbamoyl Quinolones

The compounds of this invention, herein referred to as "dithiocarbamoyl quinolones", encompass any of a variety of quinolones (and related heterocyclic moieties) having a dithiocarbamate substituent at the 1- and/or 7-position of the quinolone moiety.

The dithiocarbamoyl quinolones of this invention include compounds of the general structure:

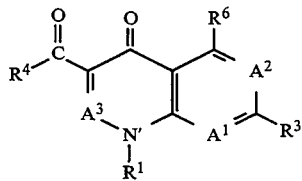

wherein
(A)
(1) $A^1$ is N or $C(R^7)$; where
(i) $R^7$ is hydrogen, hydroxy, alkoxy, nitro, cyano, halogen, alkyl, or $N(R^8)(R^9)$ (preferably hydrogen or halogen), and
(ii) $R^8$ and $R^9$ are, independently, $R^{8a}$; where $R^{8a}$ is hydrogen, alkyl, alkenyl, carbocyclic ring, or heterocyclic ring substituents; or $R^8$ and $R^9$ together comprise a heterocyclic ring including the nitrogen to which they are bonded;
(2) $A^2$ is N or (preferably) $C(R^2)$; where $R^2$ is hydrogen or (preferably) halogen;
(3) $A^3$ is N or (preferably) $C(R^5)$; where $R^5$ is hydrogen;
(4) $R^1$ is hydrogen, alkyl, a carbocyclic ring, a heterocyclic ring, alkoxy, hydroxy, alkenyl, arylalkyl, $N(R^8)(R^9)$ (preferably alkyl or a carbocyclic ring); or X;
(5) $R^3$ is hydrogen, halogen, alkyl, a carbocyclic ring, a heterocyclic ring (preferably a heterocyclic ring); or X;
(6) $R^4$ is hydroxy; and
(7) $R^6$ is hydrogen, halogen, nitro or $N(R^8)(R^9)$ (preferably hydrogen);
(B) except that
(1) when $A^1$ is $C(R^7)$, $R^1$ and $R^7$ may together comprise a heterocyclic ring including N' and $A^1$;
(2) when $A^2$ is $C(R^2)$, $R^2$ and $R^3$ may together comprise —O—$(CH_2)_n$—O—, where n is from 1 to 4;
(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and
(4) when $A^3$ is $C(R^5)$, $R^1$ and $R^5$ may together comprise a heterocyclic ring including N' and the adjacent carbon to which $R^5$ is bonded;
(C) and
(1) $R^1$ is X, $R^3$ is X, or both $R^1$ and $R^3$ are X; and
(2) X is —$R^{15}$—$N(R^{16})(R^{17})$ or —$R^{15}$—$R^{18}$—$N(R^{19})(R^{17})$, where
(a)
(1) $R^{15}$ is nil, alkyl, a carbocyclic ring, or a heterocyclic ring; and
(2) $R^{16}$ is hydrogen; alkyl; alkenyl; a carbocyclic ring; a heterocyclic ring; or
(3) when X is $R^{15}$—$N(R^{16})(R^{17})$, $R^{16}$ and $R^{15}$ may together comprise a heterocyclic ring including the nitrogen atom to which $R^{15}$ and $R^{16}$ are bonded;
(b) $R^{17}$ is C(=S)—S—M, where M is a pharmaceutically-acceptable salt or biohydrolyzable ester; and
(c)

(1) $R^{18}$ is alkyl, a carbocyclic ring, or a heterocyclic ring; and (2) $R^{19}$ is hydrogen; alkyl; alkenyl; a carbocyclic ring; a heterocyclic ring; or (3) $R^{18}$ and $R^{19}$ may together comprise a heterocyclic ring including the nitrogen atom to which $R^{18}$ and $R^{19}$ are bonded;

and pharmaceutically-acceptable salts and biohydrolyzable esters thereof, and hydrates thereof.

Definitions and Usage of Terms:

The following is a list of definitions for terms used herein.

"Heteroatom" is a nitrogen, sulfur or oxygen atom. Groups containing one or more heteroatoms may contain different heteroatoms.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Heteroalkyl" is an unsubstituted or substituted saturated chain radical having from 3 to 8 members comprising carbon atoms and one or two heteroatoms.

"Alkenyl" is an unsubstituted or substituted hydrocarbon chain radical having from 2 to 8 carbon atoms, preferably from 2 to 4 carbon atoms, and having at least one olefinic double bond.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Aryl" is an aromatic carbocyclic ring radical. Preferred aryl groups include (for example) phenyl, tolyl, xylyl, cumenyl and naphthyl.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolinyl, and tetrazolyl.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkylamino" is an amino radical having one or two alkyl substituents (i.e., —N—alkyl).

"Arylalkyl" is an alkyl radical substituted with an aryl group. Preferred arylalkyl groups include benzyl and phenylethyl.

"Arylamino" is an amine radical substituted with an aryl group (i.e., —NH—aryl).

"Aryloxy" is an oxygen radical having a aryl substituent (i.e., —O—aryl).

"Acyl" or "carbonyl" is a radical formed by removal of the hydroxy from an carboxylic acid (i.e., R—C(=O)—). Preferred alkylacyl groups include (for example) acetyl, formyl, and priopionyl.

"Acyloxy" is an oxygen radical having an acyl substituent (i.e., —O—acyl); for example, —O—C(=O)—alkyl.

"Acylamino" is an amino radical having an acyl substituent (i.e., —N—acyl); for example, —NH—C(=O)—alkyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "biohydrolyzable ester" is an ester of a dithiocarbamoyl quinolone that does not essentially interfere with the antimicrobial activity of the compounds, or that are readily metabolized by a human or lower animal subject to yield an antimicrobially-active dithiocarbamoyl quinolone. Such esters include those that do not interfere with the biological activity of quinolone antimicrobials. Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyl oxymethyl, ethoxycarbonyl oxyethyl and isopropoxycarbonyloxyethyl esters), alkoxyalkyl esters, choline esters, and alkyl acylamino alkyl esters (such as acetamidomethyl esters).

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Also, as used in defining the structure of the compounds of this invention, a particular radical may be defined for use as a substituent in multiple locations. For example, the $R^8$ substituent is defined as a potential substituent of $R^7$, but is also incorporated into the definition of other substituents (such as $R^1$, and $R^6$). As used herein, such a radical is independently selected each time it is used (e.g., $R^8$ need not be alkyl in all occurrences in defining a given compound of this invention).

Groups $A^1$, $A^2$, $A^3$, $R^1$, $R^3$, $R^4$ and $R^6$ form any of a variety of quinolone, naphthyridine or related heterocyclic moieties known in the art to have antimicrobial activity. Such moieties are well known in the art, as described in the following articles, all incorporated by reference herein: J. Wolfson et al., "The Fluoroquinolones: Structures, Mechanisms of Action and Resistance, and Spectra of Activity In Vitro", 28 *Antimicrobial Agents and Chemotherapy* 581 (1985); and T. Rosen et al., 31 *J. Med Chem.* 1586 (1988); T. Rosen et al., 31 *J. Med. Chem.* 1598 (1988); G. Klopman et al., 31 *Antimicrob. Agents Chemother.* 1831 (1987); 31:1831–1840; J. P. Sanchez et al., 31 *J. Med. Chem.* 983 (1988); J. M. Domagalia et al., 31 *J. Med. Chem.* 991 (1988); M. P. Wentland et al., in 20 *Ann. Rep. Med. Chem.* 145 (D. M. Baily, editor, 1986); J. B. Cornett et al., in 21 *Ann. Rep. Med. Chem.* 139 (D. M. Bailey, editor, 1986); P. B. Fernandes et al., in 22 *Ann. Rep. Med. Chem.* 117 (D. M. Bailey, editor, 1987); R. Albrecht, 21 *Prog. Drug Research* 9 (1977); and P. B. Fernandes et al., in 23 *Ann. Rep. Med. Chem.* (R. C. Allen, editor, 1987).

Procedures for preparing quinolones and quinolone intermediates useful in the methods of this invention are described in the following references, all incorporated by reference herein (including articles listed within these references); 21 *Progress in Drug Research*, 9–104 (1977); 31 *J. Med. Chem.*, 503–506 (1988); 32 *J. Med. Chem.*, 1313–1318 (1989); 1987 *Liebigs Ann. Chem.*, 871–879 (1987); 14 *Drugs Exptl. Clin. Res.*, 379–383 (1988); 31 *J. Med. Chem.*, 983–991 (1988); 32 *J. Med. Chem.*, 537–542 (1989); 78 *J. Pharm. Sci.*, 585–588 (1989); 26 *J. Het. Chem.*, (1989); 24 *J. Het. Chem.*, 181–185 (1987); U.S. Pat. No. 4,599,334, 35 *Chem. Pharm. Bull.*, 2281–2285 (1987); 29 *J. Med. Chem.*, 2363–2369 (1986); 31 *J. Med. Chem.*, 991–1001 (1988); 25 *J. Het. Chem.*, 479–485 (1988); European Patent Publication 266,576; European Patent Publication 251,308, 36 *Chem. Pharm. Bull.*, 1223–1228 (1988); European Patent Publication 227,088; European Patent Publication 227,039; European Patent Publication 228,661; 31 *J. Med. Chem.*, 1586–1590 (1988); 31 *J. Med. Chem.*, 1598–1611 (1988); and 23 *J. Med. Chem.*, 1358–1363 (1980).

Preferred quinolone moieties include those where $A^1$ is $C(R^7)$, $A^2$ is $C(R^2)$, and $A^3$ is $C(R^5)$ (i.e., quinolones); $A^1$ is nitrogen, $A^2$ is $C(R^2)$, and $A^3$ is $C(R^5)$ (i.e., naphthyridines); $A^1$ is $C(R^7)$, $A^2$ is $C(R^2)$, and $A^3$ is nitrogen (i.e., cinnoline acid derivatives); and where $A^1$ is nitrogen, $A^2$ is nitrogen, and $A^3$ is $C(R^5)$ (i.e., pyridopyrimidine derivatives). More preferred quinolone moieties are those where $A^1$ is $C(R^7)$, $A^2$ is $C(R^2)$, and $A^3$ is $C(R^5)$ (i.e., quinolones); and where $A^1$ is nitrogen, $A^2$ is $C(R^2)$, and $A^3$ is $C(R^5)$ (i.e., naphthyridines). Particularly preferred quinolone moieties are where $A^1$ is $C(R^7)$, $A^2$ is $C(R^2)$, and $A^3$ is $C(R^5)$ (i.e., quinolones).

$R^1$ is preferably alkyl, aryl, cycloalkyl and alkylamino. More preferably, $R^1$ is ethyl, 2-fluoroethyl, 2-hydroxyethyl, t-butyl, 4-fluorophenyl, 2,4-difluorophenyl, methylamino and cyclopropyl. Cyclopropyl is a particularly preferred $R^1$ group. Preferred quinolone moieties also include those where $A^1$ is $C(R^7)$ and $R^1$ and $R^7$ together comprise a 6-membered heterocyclic ring containing an oxygen or sulfur atom.

$R^2$ is preferably chlorine or fluorine. Fluorine is a particularly preferred $R^2$ group.

Preferred $R^3$ groups include nitrogen-containing heterocyclic rings. Particularly preferred are nitrogen-containing heterocyclic rings having from 5 to 8 members. The heterocyclic ring may contain additional heteroatoms, such as oxygen, sulfur, or nitrogen, preferably nitrogen. Such heterocyclic groups are described in U.S. Pat. No. 4,599,334, Petersen et al., issued Jul. 8, 1986; and U.S. Pat. No. 4,670,444, Grohe et al., issued Jun. 2, 1987 (both incorporated by reference herein). Preferred $R^3$ groups include unsubstituted or substituted pyridine, piperidine, morpholine, diazabicyclo[3.1.1]heptane, diazabicyclo[2.2.1]heptane, diazabicyclo[3.2.1]octane, diazabicyclo[2.2.2]octane, thiazolidine, imidazolidine, pyrrole and thiamorpholine, as well as the following particularly preferred $R^3$ groups include piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, N-methylpiperazine and 3,5-dimethylpiperazine.

Preferred dithiocarbamoyl quinolones include those having a 6-fluoroquinolone moiety or an 8-halo-6-fluoroquinolone moiety, of formula:

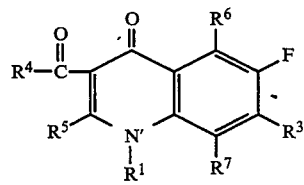

wherein, referring to formula (I), $A^2$ is $C(R^2)$ and $R^2$ is F; $A^3$ is $C(R^5)$; and $A^1$ is $C(R^7)$ where $R^7$ is hydrogen, fluorine or chlorine.

Also preferred are dithiocarbamoyl quinolones having a 1,8-naphthyridine moiety, of formula:

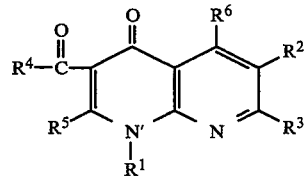

wherein, referring to formula (I), $A^1$ is N; $A^2$ is $C(R^2)$ and $A^3$ is $C(R^5)$.

Also preferred are dithiocarbamoyl quinolones having a pyridobenzoxazine or pyridobenzthiazine moiety, of formula:

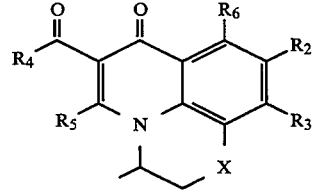

wherein, referring to formula (I), $A^1$ is $C(R^7)$; $A^2$ is $C(R^2)$; $A^3$ is $C(R^5)$; and $R^7$ and $R^1$ together comprise a linking moiety between N' and $A^1$ to form a 6-membered heterocyclic ring where X (in this formula) is oxygen or sulfur.

Also preferred are dithiocarbamoyl quinolones having an isothiazoloquinolinedione or isoxazoloquinolinedione moiety, of formula:

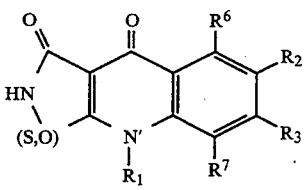

wherein, referring to formula (I), wherein $A^1$ is $C(R^7)$; $A^2$ is $C(R^2)$; $A^3$ is $C(R^5)$; and $R^4$ and $R^5$ together comprise a moiety forming a 5-membered, substituted, heterocyclic ring.

Preferred dithiocarbamoyl quinolones include the following classes of compounds.

1. $A^1$ is —$C(R^7)$—; $A^2$ is —CF—; and $A^3$ is —CH—;
2. $A^1$ is —$C(R^7)$; $A^2$ is —CF—; $A^3$ is —CH—; and $R^3$ is —$R^{15}$—$N(R^{16})(R^{17})$ or —$R^{15}$—$R^{18}$—$N(R^{19})(R^{17})$, a mercapto(thioxomethyl)amino substituted heterocyclic ring, a mercapto(thioxomethyl)amino alkyl substituted heterocyclic ring, or an N-[mercapto(thioxomethyl)] substituted heterocyclic ring;
3. $A^1$ is —$(CR^7)$—; $A^2$ is —CF—; $A^3$ is —CH—; $R^1$ is —$R^{15}$—$N(R^{16})(R^{17})$, a mercapto(thioxomethyl)amino, a mercapto(thioxomethyl)amino substituted alkyl, or a mercapto(thioxomethyl)amino substituted carbocyclic ring;
4. $A^1$ is —CH—, —CF—, —CCl—; $A^2$ is —CF—; $A^3$ is —CH—; $R^4$ is OH and pharmaceutically-acceptable salts; $R^6$ is H; $R^1$ is cyclopropyl, ethyl, 2,4-difluorophenyl, 4-fluorophenyl, or t-butyl; and $R^3$ is a 3-[mercapto(thioxomethyl)amino]-1-pyrrolidinyl group, a 3-[mercapto(thioxomethyl)aminomethyl]-1-pyrrolidinyl group, a 3-[ethyl[mercapto(thioxomethyl)]aminomethyl]-1-pyrrolidinyl group, a 3-[methyl[mercapto(thioxomethyl)]aminomethyl]-1-pyrrolidinyl group or a 4-[mercapto(thioxomethyl)]-1-piperazinyl group;
5. $A^1$ is —N—; $A^2$ is —CF—; and $A^3$ is —CH—;
6. $A^1$ is —N; $A^2$ is —CF—; $A^3$ is —CH—; and $R^3$ is —$R^{15}$—$N(R^{16})(R^{17})$ or $R^{15}$—$R^{18}$—$N(R^{19})(R^{17})$, a mercapto(thioxomethyl)amino substituted heterocyclic ring, a mercapto(thioxomethyl)amino alkyl substituted heterocyclic ring, or an N-[mercapto(thioxomethyl)] substituted heterocyclic ring
7. $A^1$ is —N—; $A^2$ is —CF—; $A^3$ is —CH—; $R^1$ is —$R^{15}$—$N(R^{16})(R^{17})$, a mercapto(thioxomethyl)amino, a mercapto(thioxomethyl)amino substituted alkyl, or a mercapto(thioxomethyl)amino substituted carbocyclic ring;
8. $A^1$ is —N—; $A^2$ is —CF—; $A^3$ is —CH—; $R^4$ is OH and pharmaceutically-acceptable salts; $R^6$ is H; $R^1$ is cyclopropyl, ethyl, 2,4-difluorophenyl, 4-fluorophenyl, or t-butyl; and $R^3$ is a 3-[mercapto(thioxomethyl)amino]-1-pyrrolidinyl group, a 3-[mercapto(thioxomethyl)aminomethyl]-1-pyrrolidinyl group, a 3-[ethyl[mercapto(thioxomethyl)]aminomethyl]-1-pyrrolidinyl group, a 3-[methyl[mercapto(thioxomethyl)]aminomethyl]-1-pyrrolidinyl group or a 4-[mercapto(thioxomethyl)]-1-piperazinyl group;
9. $A^1$ is —$C(R^7)$— and $R^7$ and $R^1$ together comprise a heterocyclic 6-membered ring including N' and $A^1$; $A^2$ is —CF—; and $A^3$ is —CH—;
10. $A^1$ is —$C(R^7)$— and $R^7$ and $R^1$ together comprise a heterocyclic 6-membered ring including N' and $A^1$; $A^2$ is —CF—; $A^3$ is —CH—; and $R^3$ is —$R^1$-5—$N(R^{16})(R^{17})$ or $R^{15}$—$R^{18}$—$N(R^{19})(R^{17})$, a mercapto(thioxomethyl)amino substituted heterocyclic ring, a mercapto(thioxomethyl)amino alkyl substituted heterocyclic ring, or an N-[mercapto(thioxomethyl)] substituted heterocyclic ring;
11. $A^1$ is —$C(R^7)$—, and $R^7$ and $R^1$ together comprise a heterocyclic, 6-membered, oxygen- or sulfur-containing ring including N' and $A^1$; $A^2$ is —CF—; $A^3$ is —CH—; $R^4$ is OH and pharmaceutically-acceptable salts; $R^6$ is H; and $R^3$ is a 3-[mercapto(thioxomethyl)amino]-1-pyrrolidinyl group, a 3-[mercapto(thioxomethyl)aminomethyl]-1-pyrrolidinyl group, a 3-[ethyl[mercapto(thioxomethyl)]aminomethyl]-1-pyrrolidinyl group, a 3-[methyl[mercapto(thioxomethyl)]aminomethyl]-1-pyrrolidinyl group or a 4-[mercapto(thioxomethyl)]-1-piperazinyl group;
12. $A^1$ is —$C(R^7)$— or —N—; $A^2$ is —CF—; and $A^3$ is —$C(R^5)$—, and $R^4$ and $R^5$ together comprise a heterocyclic ring including the carbon atoms to which $R^4$ and $R^5$ are bonded;
13. $A^1$ is —$C(R^7)$— or —N—; $A^2$ is —CF—; $A^3$ is —$C(R^5)$—, and $R^4$ and $R^5$ together comprise a heterocyclic ring including the carbon atoms to which $R^4$ and $R^5$ are bonded; and $R^3$ is —$R^1$-5—$N(R^{16})(R^{17})$ or $R^{15}$—$R^{18}$—$N(R^{19})(R^{17})$, a mercapto(thioxomethyl)amino substituted heterocyclic ring, a mercapto(thioxomethyl)amino alkyl substituted heterocyclic ring, or an N-[mercapto(thioxomethyl)] substituted heterocyclic ring;
14. $A^1$ is —$(CR^7)$— or —N—; $A^2$ is —CF—; $A^3$ is —$C(R^5)$—, and $R^4$ and $R^5$ together comprise a heterocyclic ring including the carbon atoms to which $R^4$ and $R^5$ are bonded; $R^1$ is —$R^1$-5—$N(R^{16})(R^{17})$, a mercapto(thioxomethyl)amino, a mercapto(thioxomethyl)amino substituted alkyl, or a mercapto(thioxomethyl)amino substituted carbocyclic ring; and $R^3$ is a 3-amino-1-pyrrolidinyl group, a 3-aminomethyl-1-pyrrolidinyl group, a 3-ethylaminomethyl-1-pyrrolidinyl group, a 3-methylaminomethyl-1-pyrrolidinyl group, a 4-methyl-1-piperazinyl or a 1-piperazinyl group; and
15. $A^1$ is —CH—, —CF—, —CCl— —N—; $A^2$ is —CF—; $A^3$ is —$C(R^5)$—, and $R^4$ and $R^5$ together comprise a sulfur- or oxygen-containing 5-membered heterocyclic ring including the carbon atoms to which $R^4$ and $R^5$ are bonded; $R^6$ is H; $R^1$ is cyclopropyl, ethyl, 2,4-difluorophenyl, 4-fluorophenyl, or t-butyl; and $R^3$ is a 3-[mercapto(thioxomethyl)amino]-1-pyrrolidinyl group, a 3-[mercapto(thioxomethyl)aminomethyl]-1-pyrrolidinyl group, a 3-[ethyl[mercapto(thioxomethyl)]aminomethyl]-1-pyrrolidinyl group, a 3-[methyl[mercapto(thioxomethyl)]aminomethyl]-1-pyrrolidinyl group or a 4-[mercapto(thioxomethyl)]-1-piperazinyl group.

Dithiocarbamoyl quinolones of classes 2, 3, 4, 6, 7, 8, 9, 10, 11, 13, 14 and 15 are preferred. Compounds of classes 4, 8, 11 and 15 are particularly preferred.

The compounds of this invention are also useful as intermediates in the synthesis of novel dithiocarbamoyl quinolones. Such compounds are disclosed in U.S. patent application Ser. No. 416,645, filed Oct. 10, 1989, now abandoned, incorporated by reference herein. Lactam-quinolones encompass any of a variety of lactam moieties linked, by a linking moiety, to a quinolone moiety at positions other than the 3-carboxy position.

Lactam-quinolones include compounds having the general structure:

Q-L-B wherein Q, L and B are defined as follows:
(I) Q is a structure according to Formula (I)

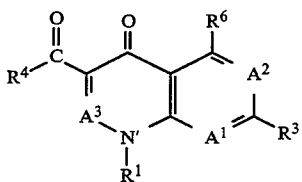

wherein
(A)
(1) $A^1$ is N or $C(R^7)$; where
  (i) $R^7$ is hydrogen, hydroxy, alkoxy, nitro, cyano, halogen, alkyl, or $N(R^8)(R^9)$ (preferably hydrogen or halogen), and
  (ii) $R^8$ and $R^9$ are, independently, $R^{8a}$, where $R^{8a}$ is hydrogen, alkyl, alkenyl, a carbocyclic ring, or a heterocyclic ring substituent; or $R^8$ and $R^9$ together comprise a heterocyclic ring including the nitrogen to which they are bonded;
(2) $A^2$ is N or $C(R^2)$ (preferably $C(R^2)$); where $R^2$ is hydrogen or halogen;
(3) $A^3$ is N or (preferably) $C(R^5)$; where $R^5$ is hydrogen;
(4) $R^1$ is hydrogen or $R^{15}$, where $R^{15}$ is (for this formula, only) alkyl, a carbocyclic ring, a heterocyclic ring, alkoxy, hydroxy, alkenyl, arylalkyl, or $N(R^8)(R^9)$ (preferably alkyl or a carbocyclic ring);
(5) $R^3$ is hydrogen, halogen, or $R^{16}$, where $R^{16}$ (for this formula, only) is alkyl, a carbocyclic ring, or a heterocyclic ring (preferably a heterocyclic ring);
(6) $R^4$ is hydroxy; and
(7) $R^6$ is hydrogen, halogen, nitro, or $N(R^8)(R^9)$ (preferably hydrogen);
(B) except that
(1) when $A^1$ is $C(R^7)$, $R^1$ and $R^7$ may together comprise a heterocyclic ring including N' and $A^1$;
(2) when $A^2$ is $C(R^2)$, $R^2$ and $R^3$ may together comprise —O—$(CH_2)_n$—O—, where n is an integer from 1 to 4;
(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and
(4) when $A^3$ is $C(R^5)$, $R^1$ and $R^5$ may together comprise a heterocyclic ring including N' and the adjacent carbon to which $R^5$ is bonded;
(C) and either
(1) $R^1$ is $R^{15}$ and is a substituent moiety of L; or
(2) $R^3$ is $R^{16}$ and is a substituent moiety of L;
(II) B is a structure according to Formula (II), where L is bonded to $R^{14}$:

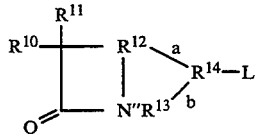

wherein
(A) $R^{10}$ is hydrogen, halogen, alkyl, alkenyl, heteroalkyl, a carbocyclic ring, a heterocyclic ring, $R^{8a}$—O—, $R^{8a}CH=N$—, $(R^8)(R^9)N$—, $R^{17}$—C(=CHR$^{20}$)—C(=O)NH—, or (preferably) $R^{17}$—C(=NO—R$^{19}$)—C(=O)NH—, or $R^{18}$—$(CH_2)_m$—C(=O)NH—; where
(1) m is an integer from 0 to 9 (preferably from 0 to 3);
(2) $R^{17}$ is (for this formula, only) hydrogen, alkyl, alkenyl, heteroalkyl, heteroalkenyl, a carbocyclic ring, or a heterocyclic ring (preferably alkyl, a carbocyclic ring, or a heterocyclic ring);
(3) $R^{18}$ is (for this formula, only) $R^{17}$, —$Y^1$, or —$CH(Y^2)(R^{17})$;
(4) $R^{19}$ is (for this formula, only) $R^{17}$, arylalkyl, heteroarylalkyl, —$C(R^{22})(R^{23})COOH$, —C(=O)O—$R^{17}$, or —C(=O)NH—$R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded (preferably $R^{17}$ or —$C(R^{22})(R^{23})COOH$)
(5) $R^{20}$ is $R^{19}$, halogen, —$Y^1$, or —$CH(Y^2)(R^{17})$ (preferably $R^{19}$ or halogen);
(6) $Y^1$ is —C(=O)O$R^{21}$, —C(=O)$R^{21}$, —N(R$^{24}$)$R^{21}$, or (preferably) —S(O)$_p R^{29}$ or —O$R^{29}$; and $Y^2$ is $Y^1$ or —OH, —SH, or —SO$_3$H;
(a) p is an integer from 0 to 2 (preferably 0);
(b) $R^{24}$ is hydrogen; alkyl; alkenyl; heteroalkyl; heteroalkenyl; a carbocyclic ring; a heterocyclic ring; —SO$_3$H; —C(=O)R$^{25}$; or, when $R^{18}$ is —CH(Y—R$^{21}$)(R$^{17}$), $R^{24}$ may comprise a moiety bonded to $R^{21}$ to form a heterocyclic ring; and
(c) $R^{25}$ is $R^{17}$, NH(R$^{17}$), N(R$^{17}$)(R$^{26}$), O(R$^{26}$), or S(R$^{26}$) (preferably $R^{17}$, NH(R$^{17}$) or N(R$^{17}$)(R$^{26}$)); where $R^{26}$ is alkyl, alkenyl, a carbocyclic ring, a heterocyclic ring or (preferably) when $R^{25}$ is N(R$^{17}$)(R$^{26}$), $R^{26}$ may comprise a moiety bonded to $R^{17}$ to form a heterocyclic ring; and
(7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when Y is N(R$^{24}$) and $R^{21}$ is $R^{29}$, $R^{21}$ and $R^{24}$ may together comprise a carbocyclic ring or a heterocyclic ring including the nitrogen atom to which $R^{29}$ is bonded (preferably hydrogen, alkyl, a carbocyclic ring or a heterocyclic ring);
(B) $R^{11}$ is hydrogen, halogen, alkoxy, or $R^{27}C(=O)NH$— (preferably hydrogen or alkoxy), where $R^{27}$ is hydrogen or alkyl (preferably hydrogen);
(C) bond "a" is a single bond or is nil; and bond "b" is a single bond, a double bond, or is nil; except bond "a" and bond "b" are not both nil;

(D) $R^{12}$ is —C($R^{8a}$)—, or —CH$_2$—$R^{28}$— (preferably —C($R^{8a}$)—); where $R^{28}$ is —C($R^8$), —O—, or —N—, and $R^{28}$ is directly bonded to N″ in Formula (II) to form a 5-membered ring; except, if bond "a" is nil, then $R^{12}$ is
  (1) (preferably) —C($R^{8a}$)($X^1$)—, where
    (i) $X^1$ is —$R^{21}$; —O$R^{30}$; —S(O)$_r R^{30}$, where r is an integer from 0 to 2 (preferably 0); —OC(=O)$R^{30}$; or N($R^{30}$)$R^{31}$; and
    (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or
  (2) —CH$_2$—$R^{32}$—; where $R^{32}$ is —C($R^8$)($R^{21}$), —O—, or —N$R^8$, and $R^{32}$ is directly bonded to N″ in Formula (II) to form a 5-membered ring;

(E)
  (1) if bond "b" is a single bond, $R^{13}$ is preferably —CH($R^{33}$)—; or, —C(O)NHSO$_2$—, if bond "a" is nil; or —C*($R^{33}$)—, if $R^{14}$ contains a $R^{36}$ moiety; where $R^{33}$ is hydrogen or COOH (preferably COOH), and C* is linked to $R^{36}$ to form a 3-membered ring;
  (2) if bond "b" is a double bond, $R^{13}$ is —C($R^{33}$)=; or
  (3) if bond "b" is nil, $R^{13}$ is hydrogen, —SO$_3$H, —PO(O$R^{34}$)OH, —C(O)NHSO$_2$N($R^{34}$)($R^{35}$), —OSO$_3$H, —CH($R^{35}$)COOH, or —OCH($R^{34}$)COOH (preferably —SO$_3$H, or —C(O)NHSO$_2$N($R^{34}$)($R^{35}$); where $R^{34}$ is hydrogen, alkyl, alkenyl, a carbocyclic ring, or a heterocyclic ring; and $R^{35}$ is hydrogen, alkyl, alkenyl, or —NH$R^{8a}$; or (preferably), if $R^{13}$ is —C(O)NHSO$_2$N($R^{34}$)($R^{35}$), $R^{34}$ and $R^{35}$ may together comprise a heterocyclic ring including the nitrogen to which $R^{34}$ and $R^{35}$ are bonded; and (F)
  (1) if bond "a" or bond "b" is nil, then $R^{14}$ is nil and L is bonded directly to $R^{12}$ or $R^{13}$;
  (2) if bond "a" and "b" are single bonds, $R^{14}$ is —W—C‴=C($R^{8a}$)—$R^{37}$—, or —W—C‴($R^{36}$)—$R^{37}$—; or
  (3) (preferably) if bond "a" is a single bond and bond "b" is a double bond, $R^{14}$ is —C($R^{8a}$)($R^{38}$)—W—C‴—$R^{37}$—; or (preferably) —W—C(-$R^{8a}$)($R^{38}$)—C‴—$R^{37}$—, or —W—C‴—$R^{37}$—; where
    (a) W is 0; S(O)s, where s is an integer from 0 to 2 (preferably 0); or C($R^{38}$), where $R^{38}$ is hydrogen, alkyl or alkoxy;
    (b) $R^{36}$ hydrogen; alkyl; alkenyl; —COOH; or, if $R^{13}$ is —C*($R^{33}$), $R^{36}$ may be linked to C* to form a 3-membered carbocyclic ring;
    (c) $R^{37}$ is nil, alkyl, alkenyl, a carbocyclic ring, or a heterocyclic ring; and
    (d) C‴ is directly bonded to $R^{13}$ to form a 5- or 6-membered ring,
and
  (III) L links Q to B; and L is L′, —$X^2_r$—$R^{39}$—L′, or —$X^3_r$—$R^{39}$—L′; where L′ is —$X^4$—C(=$Y^3$)—Z—Q″;
    (1) $R^{39}$ is alkyl, alkenyl, heteroalkyl, heteroalkenyl, a carbocyclic ring, or a heterocyclic ring (preferably alkyl or alkenyl);
    (2) $X^2$ is oxygen, or S(O)$_v$, where v is an integer from 0 to 2 (preferably 0);
    (3) $X^3$ is nitrogen; N($R^{40}$); N+($R^{41}$)($R^{42}$); or $R^{43}$—N($R^{41}$); and is linked to $R^{14}$ by a single or double bond; or, if $R^{14}$ is nil, $X^3$ is linked to B by a single or double bond (preferably $X^3$ is nitrogen, N($R^{40}$) or N+($R^{41}$)($R^{42}$)); where
      (a) $R^{40}$ is $R^{8a}$; —O$R^{8a}$; or —C(=O)$R^{8a}$; (preferably $R^8$);
      (b) $R^{41}$ and $R^{42}$ are, independently, hydrogen; alkyl; alkenyl; carbocyclic rings; heterocyclic rings; or, (preferably) together with Q″, comprise a heterocyclic ring as $R^{15}$ or $R^{16}$;
      (c) $R^{43}$ is N($R^{41}$), oxygen or sulfur;
    (4) $X^4$ is sulfur;
    (5) $Y^3$ is sulfur;
    (6) Z is nitrogen;
    (7) Q″ is $R^{15}$ or $R^{16}$; or together with Z, is an $R^{15}$ or $R^{16}$ group;
and pharmaceutically-acceptable salts and biohydrolyzable esters thereof, and hydrates thereof.

Preferred lactam-containing moieties include cephems, isocephems, iso-oxacephems, oxacephems, carbacephems, penicillins, penems, carbapenems, and monocyclic beta-lactams. Particularly preferred are cephems, penems, carbapenems and monocyclic beta-lactams.

$R^{10}$, in formula (II), is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity.) This "active" position is beta (i.e., 7-beta) for cephems, oxacephems and carbacephems (for example). The active position is alpha for penems, carbapenems, clavems and clavams. Appropriate $R^{10}$ groups will be apparent to one of ordinary skill in the art.

Compositions

The compositions of this invention comprise:
(a) a safe and effective amount of a dithiocarbamoyl quinolone; and
(b) a pharmaceutically-acceptable carrier.

A "safe and effective amount" of a dithiocarbamoyl quinolone is an amount that is effective, to inhibit microbial growth at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the dithiocarbamoyl quinolone therein, and the dosage regimen desired for the composition.

The compositions of this invention are preferably provided in unit dosage form. As used herein, a "unit dosage form" is a composition of this invention containing an amount of a dithiocarbamoyl quinolone that is suitable for administration to a human or lower animal subject, in a single dose, according to good medical practice. These compositions preferably contain from about 30 mg to about 20,000 mg, more preferably from about 50 mg (milligrams) to about 7000 mg, more preferably from about 500 mg to about 3500 mg, of a dithiocarbamoyl quinolone.

The compositions of this invention may be in any of a variety of forms, suitable (for example) for oral, rectal, topical or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the antimicrobial activity of the dithiocarbamoyl quinolone. The amount of carrier employed in conjunction with the dithiocarbamoyl quinolone is sufficient to provide a practical quantity of material for administration per unit dose of the dithiocarbamoyl quinolone. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight by the total composition.

Various oral dosage forms can be used, including such solid forms as tablets, capsules, granules and bulk powders. These oral forms comprise a safe and effective amount, usually at least about 5%, and preferably from about 25% to about 50%, of the dithiocarbamoyl quinolone. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the dithiocarbamoyl quinolone. Suitable carriers for topical administration preferably remain in place on the skin as a continuous film, and resist being removed by perspiration or immersion in water. Generally, the carrier is organic in nature and capable of having dispersed or dissolved therein the dithiocarbamoyl quinolone. The carrier may include pharmaceutically-acceptable emolients, emulsifiers, thickening agents, and solvents.

Methods of Administration

This invention also provides methods of treating or preventing an infectious disorder in a human or other animal subject, by administering a safe and effective amount of a dithiocarbamoyl quinolone to said subject. As used herein, an "infectious disorder" is any disorder characterized by the presence of a microbial infection. Preferred methods of this invention are for the treatment of bacterial infections. Such infectious disorders include (for example) central nervous system infectic , external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients (such as patients receiving cancer chemotherapy, or organ transplant patients).

The dithiocarbamoyl quinolones and compositions of this invention can be administered topically or systemically. Systemic application includes any method of introducing the dithiocarbamoyl quinolone into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific dithiocarbamoyl quinolone used, the resistance pattern of the infecting organism to the dithiocarbamoyl quinolone used, the ability of the dithiocarbamoyl quinolone to reach minimum inhibitory concentrations at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 75 mg to about 30,000 mg, more preferably from about 100 mg to about 20,000 mg, more preferably from about 500 mg to about 3500 mg, of dithiocarbamoyl quinolone are administered per day. Treatment regimens preferably extend from about 1 to about 56 days, preferably from about 7 to about 28 days, in duration. Prophylactic regimens (such as avoidance of opportunistic infections in immunocompromised patients) may extend 6 months, or longer, according to good medical practice.

A preferred method of parenteral administration is through intramuscular injection. As is known and practiced in the art, all formulations for parenteral administration must be sterile. For mammals, especially humans, (assuming an approximate body weight of 70 kilograms) individual doses of from about 100 mg to about 7000 mg, preferably from about 500 mg to about 3500 mg, are acceptable.

A preferred method of systemic administration is oral. Individual doses of from about 100 mg to about 2500 mg, preferably from about 250 mg to about 1000 mg are preferred.

Topical administration can be used to deliver the dithiocarbamoyl quinolone systemically, or to treat a local infection. The amounts of dithiocarbamoyl quinolone to be topically administered depends upon such factors as skin sensitivity, type and location of the tissue to be treated, the composition and carrier (if any) to be administered, the particular dithiocarbamoyl quinolone to be administered, as well as the particular disorder to be treated and the extent to which systemic (as distinguished from local) effects are desired.

The following non-limiting examples illustrate the compounds, compositions, processes, and uses of the present invention.

EXAMPLE 1

1-Cyclopropyl-6-fluoro-1,4-dihydro-7-[4-(mercapto)-thioxomethyl]-1-piperazinyl]-4-oxo-3-quinoline carboxylic acid, Disodium Salt is made by the following procedure.

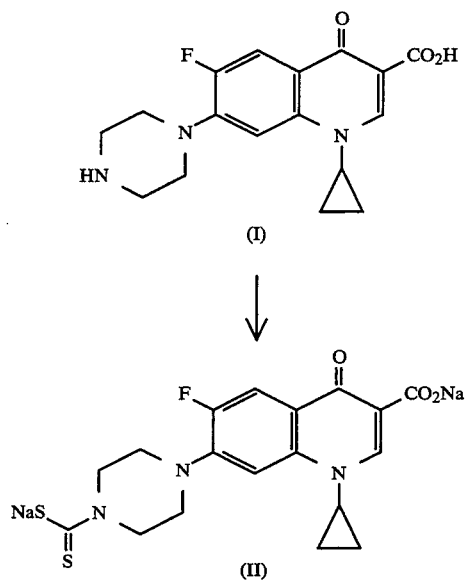

To a suspension of approximately 5.0 gm 1-cyclopropyl-6-fluoro-1,4-dihydro-4-oxo-7-(1-piperazinyl)-3-quinoline carboxylic acid (I, prepared according to K. Grohe, et al., Ger. Offen. DE 3142854) in 7.5 ml of 4N sodium hydroxide solution and 10 ml water at approximately 4° C. is added dropwise with stirring approximately 0.9 ml carbon disulfide. The reaction is stirred in the cold for approximately 2 hours after which an additional 0.9 ml aliquot of carbon disulfide is added. The reaction is allowed to warm to room temperature as it stirred for an additional 16 hours. The mixture is then cooled to approximately 10° C. and diluted with acetone to precipitate the product which is collected by filtration, washed with acetone and dried to obtain product (II).

Similarly, the following dithiocarbamoyl quinolones are made, with substantially similar results.

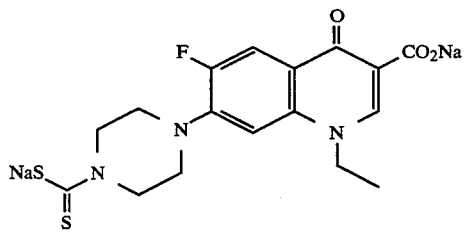

using the quinolone 1-ethyl-6-fluoro-1,4-dihydro-4-oxo-7-(1-piperazinyl)-3-quinoline carboxylic acid (prepared according to H. Koga, et. al., J. Med. Chem., 1980, 23, 1358).

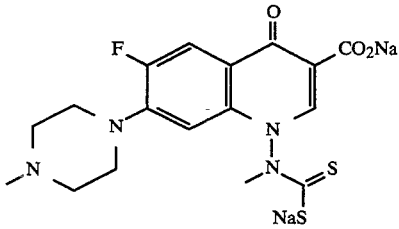

using the quinolone 6-fluoro-1,4-dihydro-1-methylamino-7-(4-methyl-1-piperazinyl)-4-oxo-3-quinoline carboxylic acid (prepared according to M. P. Wentland, et. al., J. Med. Chem., 1984, 27, 1103).

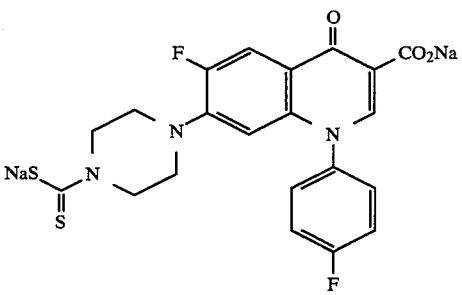

using the quinolone 6-fluoro-1-(4-fluorophenyl)-1,4-dihydro-4-oxo-7-(1-piperazinyl)-3-quinoline carboxylic acid (prepared according to D. T. W. Chu, et. al., J. Med. Chem., 1985, 28, 1558).

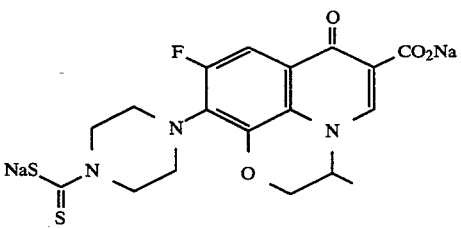

using the quinolone 9-fluoro-4,7-dihydro-3-methyl-10-(1-piperazinyl)-7-oxo-2H-pyrido[1,2,3-de]-1,4-benzoxazine-6-carboxylic acid (prepared according to I. Hayakawa, et. al., Chem. Pharm. Bull., 1984, 32, 4907).

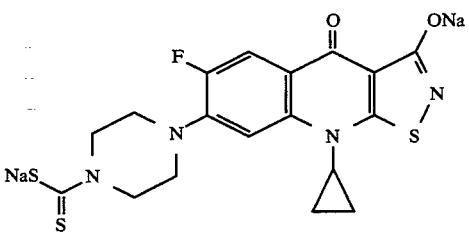

using the quinolone 9-cyclopropyl-6-fluoro-2,3,4,9-tetrahydro-7-(1-piperazinyl)isothiazolo[5,4-b]quinoline-3,4-dione (prepared according to D. T. W. Chu, EP 227,088).

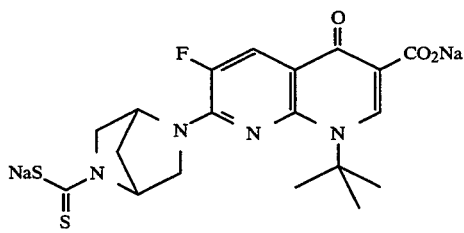

using the naphthyridinone 7-(2,5-diazabicyclo[2.2.1-]heptan-2-yl)-1-(1,1-dimethylethyl)-6-fluoro-1,4-dihydro-4-oxo-1,8-naphthyridine-3-carboxylic acid (prepared according to A. Weber, et. al., EP 266576).

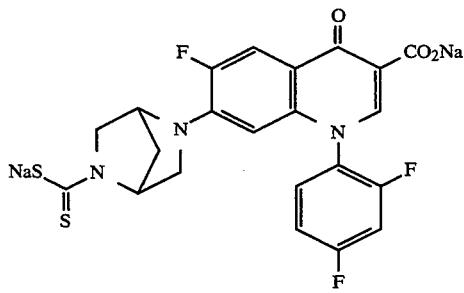

using the quinolone 7-(2,5-diazabicyclo[2.2.1]heptan-2-yl)-6-fluoro-1-(4-fluorophenyl)-1,4-dihydro-4-oxo-3-quinoline carboxylic acid (prepared according to F. Sauter, et al., EP 251,308).

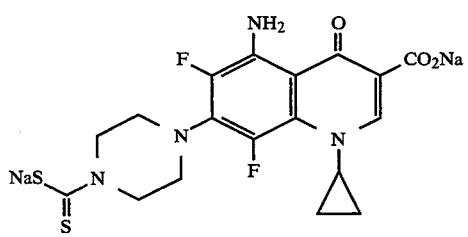

using the quinolone 5-amino-1-cyclopropyl-6,8-difluoro-4-oxo-7-(1-piperazinyl)-3-quinoline carboxylic acid (prepared according to J. M. Domagalia, et. al., J. Med. Chem., 1988, 31, 506).

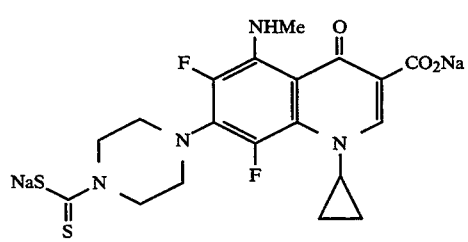

using the quinolone 1-cyclopropyl-6,8-difluoro-5-(methylamino)-4-oxo-7-(1-piperazinyl)-3-quinoline carboxylic acid (prepared according to J. M. Domagalia, et. al., J. Med. Chem., 1988, 31, 506).

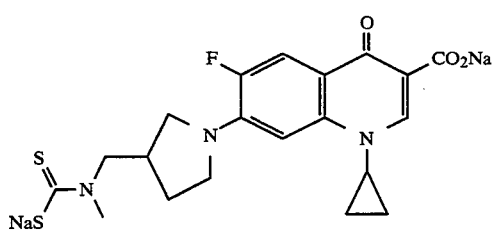

using the quinolone 1-cyclopropyl-6-fluoro-1,4-dihydro-7-[[3-(methylamino)methyl]-1-pyrrolidinyl]-4-oxo-3-quinoline carboxylic acid (prepared according to J. P. Sanchez, et. al., J. Med. Chem., 1988, 31, 983).

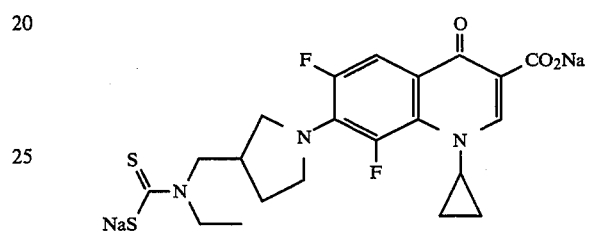

using the quinolone 1-cyclopropyl-7-[[3-(ethylamino)-methyl]-1-pyrrolidinyl]-6,8-difluoro-1,4-dihydro-4-oxo-3-quinoline carboxylic acid (prepared according to J. P. Sanchez, et. al., J. Med. Chem., 1988, 31, 983).

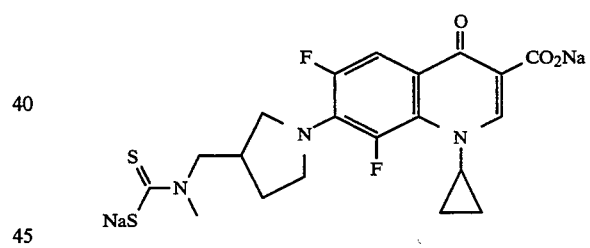

using the quinolone 1-cyclopropyl-6,8-difluoro-1,4-dihydro-7-[[3-(methylamino)methyl]-1-pyrrolidinyl]-4-oxo-3-quinoline carboxylic acid (prepared according to J. P. Sanchez, et. al., J. Med. Chem., 1988, 31, 983).

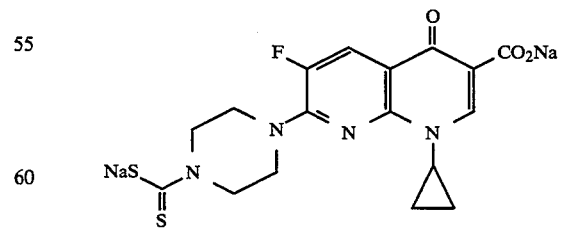

using the naphthyridinone 1-cyclopropyl-6-fluoro-1,4-dihydro-4-oxo-7-(1-piperazinyl)-1,8-naphthyridine-3-carboxylic acid (prepared according to D. Bouzard, et. al., J. Med. Chem., 1989, 32, 537).

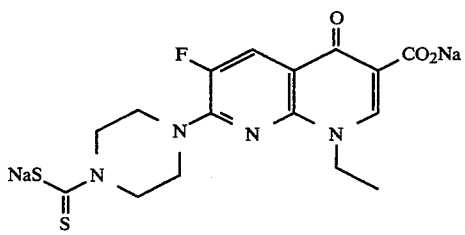

using the naphthyridinone 1-ethyl-6-fluoro-1,4-dihydro-4-oxo-7-(1-piperazinyl)-1,8-naphthyridine-3-carboxylic acid (prepared according to D. Bouzard, et. al., J. Med. Chem., 1989, 32, 537).

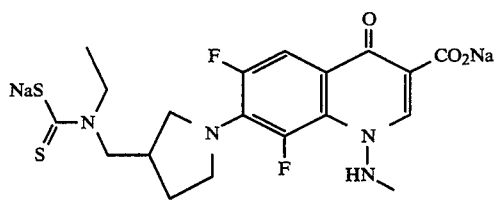

using the quinolone 7-[[3-(ethylamino)methyl]-1-pyrrolidinyl]-6,8-difluoro-1,4-dihydro-1-methylamino-4-oxo-3-quinolone carboxylic acid (prepared according to J. M. Domagalia, et. al., J. Med. Chem., 1988, 31, 991).

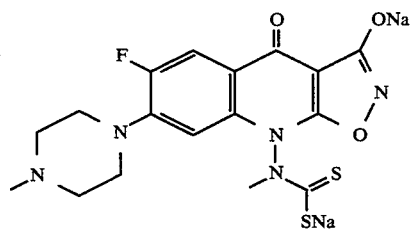

using the quinolone 6-fluoro-2,3,4,9-tetrahydro-9-methylamino-7-(4-methyl-1-piperazinyl)isothiazolo[5,4-b]quinoline-3,4-dione (prepared according to D. T. W. Chu, EP 227,088).

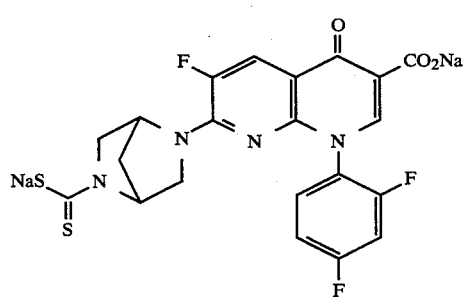

using the naphthyridinone 7-(2,5-diazabicyclo[2.2.1-]heptan-2-yl)-6-fluoro-1-(difluorophenyl)-1,4-dihydro-4-oxo-1,8-naphthyridine-3-carboxylic acid (prepared according to T. Rosen, et. al., J. Med. Chem., 1988, 31, 1598).

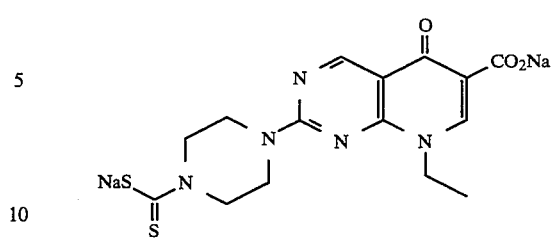

using the quinolone 8-ethyl-5,8-dihydro-5-oxo-2-(1-piperazinyl)pyrido[2,3-d]pyrimidine-6-carboxylic acid (prepared according to M. Matsumoto, J. Med. Chem., 1975, 18, 74).

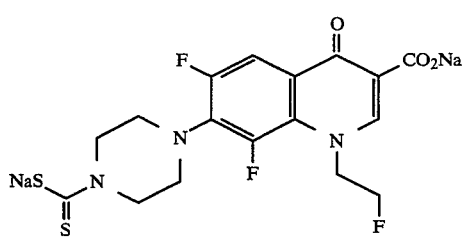

using the quinolone 6,8-difluoro-1-(2-fluoroethyl)-1,4-dihydro-4-oxo-7-(1-piperazinyl)3-quinoline carboxylic acid (prepared according to T. Irikura, et al., Pat. Specif. (Aust.) AU 537,813).

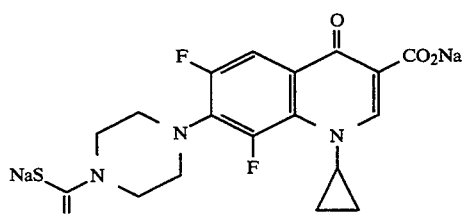

using the quinolone 1-cyclopropyl-6,8-difluoro-1,4-dihydro-4-oxo-7-(1-piperazinyl)-3-quinoline carboxylic acid (prepared according to J. P. Sanchez, et. al., J. Med. Chem., 1988, 31, 983).

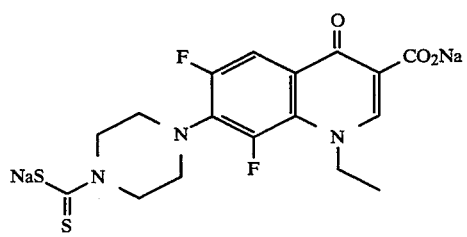

using the quinolone 1-ethyl-6,8-difluoro-1,4-dihydro-4-oxo-7-(1-piperazinyl)-3-quinoline carboxylic acid (prepared according to T. Irikura, et al., Ft. Demande FR 2,463,771).

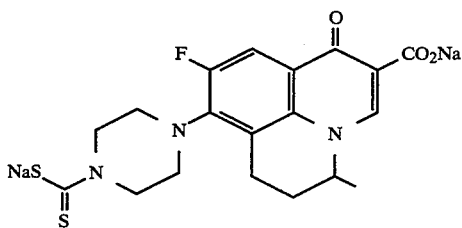

using the quinolone 9-fluoro-6,7-dihydro-5-methyl-1-oxo-8-(1-piperazinyl)-1H,5H-benzo(ij)quinolizine-2-carboxylic acid (prepared according to H. Ishikawa, et al., Get. Often. DE 2,914,258).

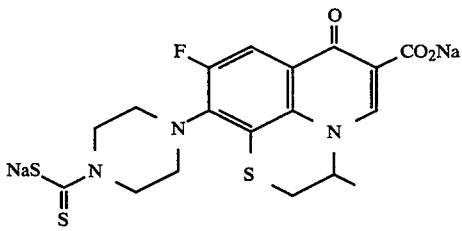

using the quinolone 9-fluoro-4,7-dihydro-3-methyl-10-(1-piperazinyl)-7-oxo-2H-pyrido[1,2,3-de]-1,4-benzthiazine-6-carboxylic acid (prepared according to I. Hayakawa, et. al., Chem. Pharm. Bull., 1984, 32, 4907).

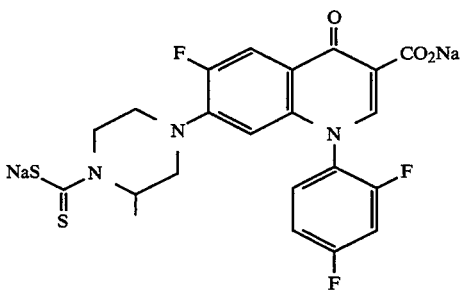

using the quinolone 6-fluoro-1-(2,4-difluorophenyl)-1,4-dihydro-7-(3-methyl-1-piperazinyl)-4-oxo-3-quinoline carboxylic acid (prepared according to H. Narita, et al., Yakugaku Zasshi, 1986, 106, 795).

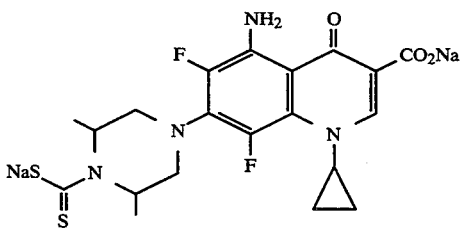

using the quinolone 5-amino-1-cyclopropyl-7-(3,5-dimethyl-1-piperazinyl)-6,8-difluoro-1,4-dihydro-4-oxo-3-quinoline carboxylic acid (prepared according to J. Matsumoto, et al., Eur. Pat. Appl. EP 221,463).

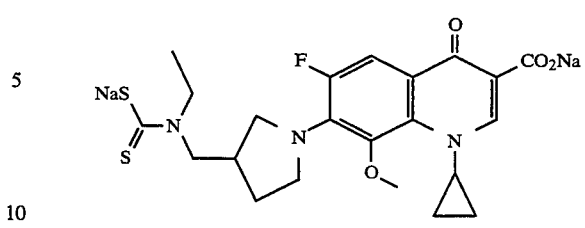

using the quinolone 1-cyclopropyl-7-[3-[(ethylamino)methyl]-1-pyrrolidinyl]-6-fluoro-1,4-dihydro-8-methoxy-4-oxo-3-quinoline carboxylic acid (prepared according to K. Masuzawa, et al., Eur. Pat. Appl. EP 230,295).

EXAMPLE 2

1-Cyclopropyl-6-fluoro-1,4-dihydro-7-[3-[(mercapto)thioxomethylamino]-1-pyrrolidinyl]-4-oxo-3-quinoline carboxylic acid, disodium salt is made by the following procedure.

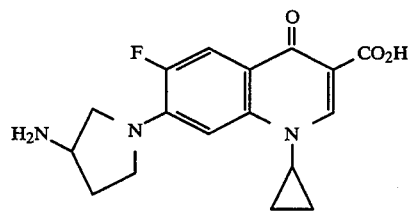

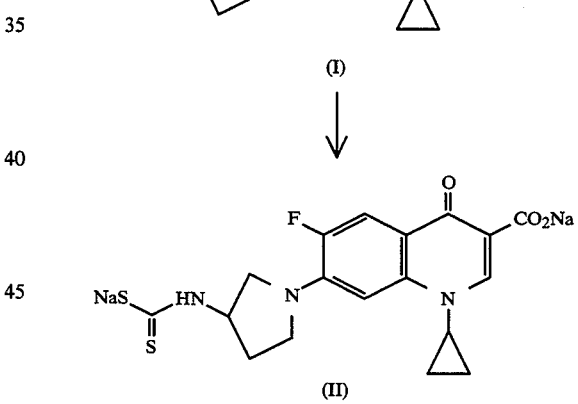

To a solution of 1.0 gm 7-(3-amino-1-pyrrolidinyl)-1-cyclopropyl-6-fluoro-1,4-dihydro-4-oxo-3-quinoline carboxylic acid (I, prepared according to J. P. Sanchez, et al., J. Med. Chem., 1988, 31, 983) in 2 ml water and approximately 0.2 ml 4N sodium hydroxide solution is added 0.2 ml carbon disulfide. The reaction is then heated at approximately 40°–45° C. for 1.5 hours, after which an additional 0.2 ml aliquot of carbon disulfide is added and the reaction is heated for an additional 1.5 hours. The solution is then cooled and acetone is added to precipitate the product which is collected, washed with acetone and dried to yield product (II).

Similarly, the following dithiocarbamoyl quinolones are made, with substantially similar results.

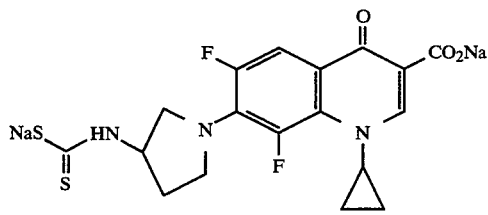

using the quinolone 7-(3-aminopyrrolidinyl)-1-cyclopropyl-6,8-difluoro-1,4-dihydro-4-oxo-3-quinoline carboxylic acid (prepared according to J. P. Sanchez, et. al., J. Med. Chem., 1988, 31, 983).

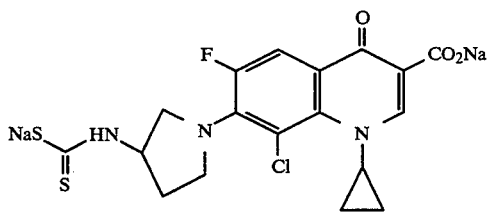

using the quinolone 7-(3-aminopyrrolidinyl)-1-chloro-1-cyclopropyl-6-fluoro-1,4-dihydro-4-oxo-3-quinoline carboxylic acid (prepared according to J. P. Sanchez, et. al., J. Med. Chem., 1988, 31, 983).

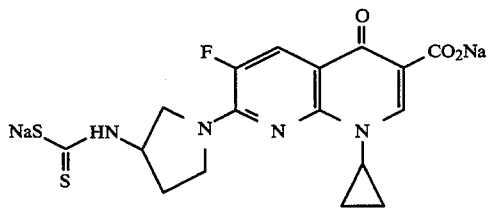

using the naphthyridinone 7-(3-aminopyrrolidinyl)-1-cyclopropyl-6fluoro1,4-dihydro-4-oxo-1,8-naphthyridine-3-carboxylic acid (prepared according to J. P. Sanchez, et. al., J. Med. Chem., 1988, 31, 983).

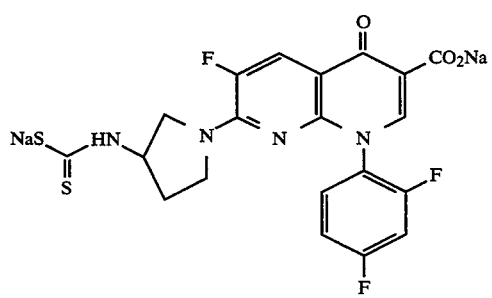

using the naphthyridinone 7-(3-aminopyrrolidinyl)-1-(2,4-difluorophenyl)-6-fluoro1,4-dihydro-4-oxo-1,8-naphthyridine-3-carboxylic acid (prepared according to D. T. W. Chu, et. al., J. Med. Chem., 1986, 29, 2363).

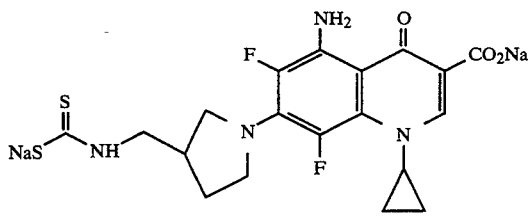

using the quinolone 5-amino-7-[(3-aminomethyl)-1-pyrrolidinyl]-1-cyclopropyl-6,8-difluoro-4-oxo-3-quinoline carboxylic acid (prepared according to J. M. Domagalia, et. al., J. Med. Chem., 1988, 31, 506).

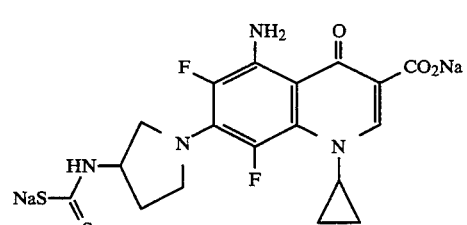

using the quinolone 5-amino-7-(3-amino-1-pyrrolidinyl)-1-cyclopropyl-6,8-difluoro-4-oxo-3-quinoline carboxylic acid (prepared according to J. M. Domagalia, et. al., J. Med. Chem., 1988, 31, 506).

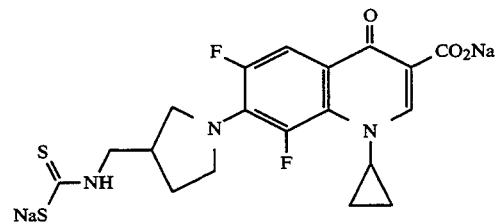

using the quinolone 7-[(3-aminomethyl)-1-pyrrolidinyl]-1-cyclopropyl-6,8-difluoro-1,4-dihydro-4-oxo-3-quinoline carboxylic acid (prepared according to J. P. Sanchez, et. al., J. Med. Chem., 1988, 31, 983).

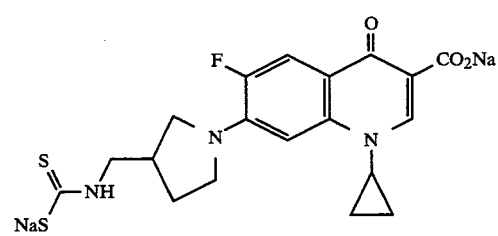

using the quinolone 7-[(3-aminomethyl)-1-pyrrolidinyl]-1-cyclopropyl-6-fluoro-1,4-dihydro-4-oxo-3-quinoline carboxylic acid (prepared according to J. P. Sanchez, et. al., J. Med. Chem., 1988, 31, 983).

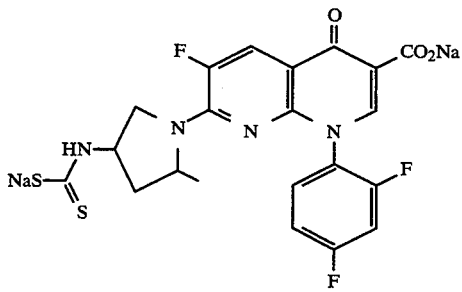

using the naphthyridinone 7-(3-amino-5-methyl-1-pyrrolidinyl)-6-fluoro-1-(difluorophenyl)-1,4-dihydro-4-oxo-1,8-naphthyridine-3-carboxylic acid (prepared according to T. Rosen, et. al., J. Med. Chem., 1988, 31, 1598).

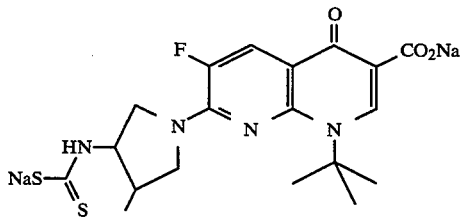

using the naphthyridinone 7-(3-amino-4-methyl-1-pyrrolidinyl)-1-(1,1-dimethylethyl)-6-fluoro-1,4-dihydro-4-oxo-1,8-naphthyridine- 3-carboxylic acid (prepared according to A. Weber, et. al., EP 266,576).

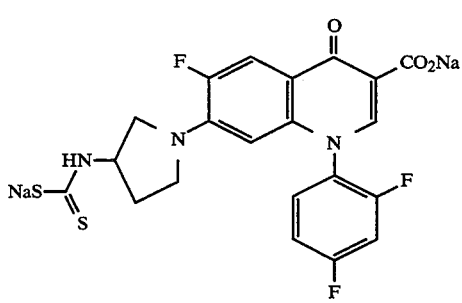

using the quinolone 7-(3-amino-1-pyrrolidinyl)-6-fluoro-1-(2,4-difluorophenyl)-1,4-dihydro-4-oxo-3-quinoline carboxylic acid (prepared according to H. Narita, et al., Yakugaku Zasshi, 1986, 106, 795).

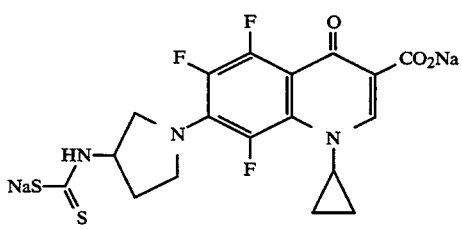

using the quinolone 7-(3-amino-1-pyrrolidinyl)-1-cyclopropyl-5,6,7-trifluoro-1,4-dihydro-4-oxo-3-quinoline carboxylic acid (prepared according to K. Miyamata, et al., Jpn. Kokai Tokkyo Koho JP 62/226962).

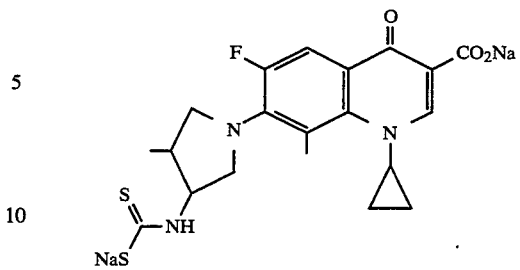

using the quinolone 7-(3-amino-4-methyl-1-pyrrolidinyl)-1-cyclopropyl-6-fluoro-1,4-dihydro-8-methyl-4-oxo-3-quinoline carboxylic acid (prepared according to the procedure in Neth. Appl. NL 87/471).

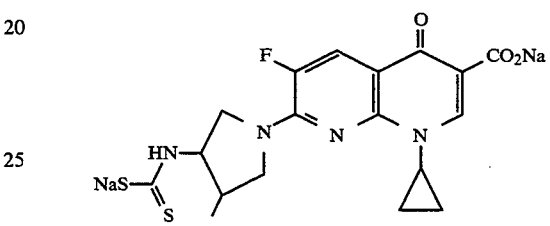

using the naphthyridinone 7-(3-amino-4-methyl-1-pyrrolidinyl)-1-cyclopropyl-6-fluoro-1,4-dihydro-4-oxo-1,8-naphthyridine-3-carboxylic acid (prepared according to J. Matsumoto, et al., Eur. Pat. Appl. EP 132,845).

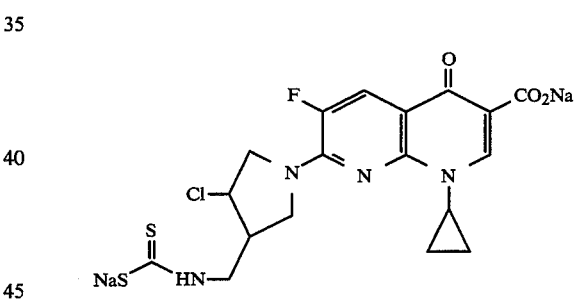

using the naphthyridinone 7-(3-aminomethyl-4-chloro-1-pyrrolidinyl)-1-cyclopropyl-6-fluoro-1,4-dihydro-4-oxo-1,8-naphthyridine- 3-carboxylic acid (prepared according to J. Matsumoto, et al., Eur. Pat. Appl. EP 191,451).

The following other dithiocarbamoyl quinolones are also made by the general procedure of this Example and Example 1, with substantially similar results.

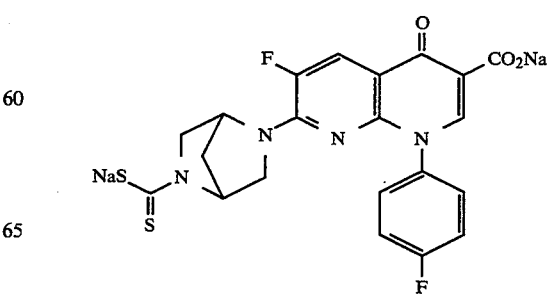

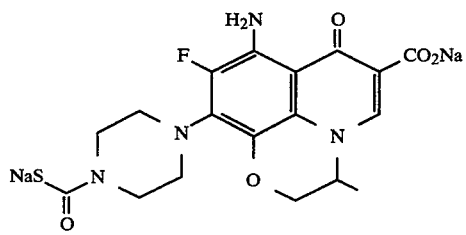
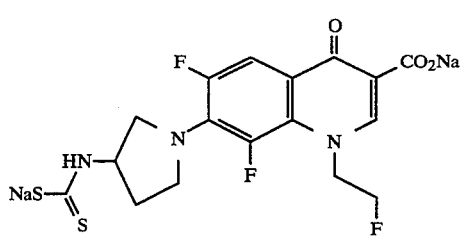
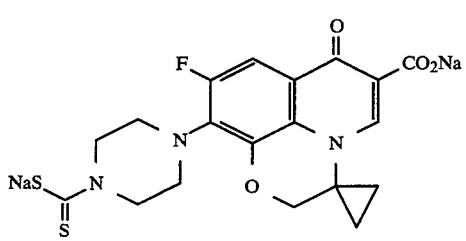
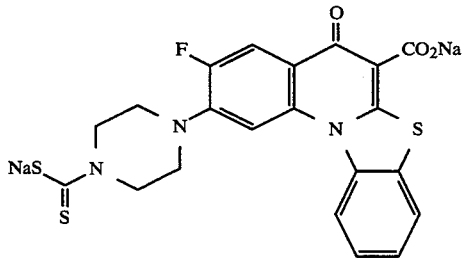
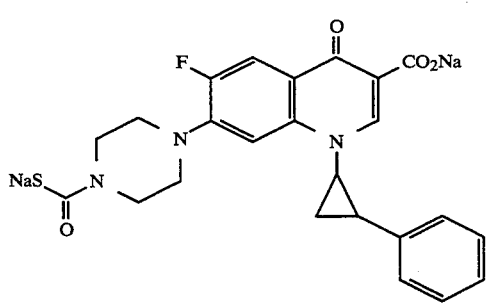
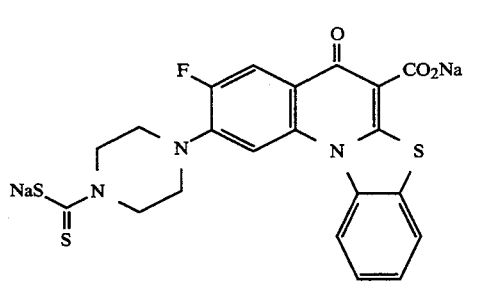
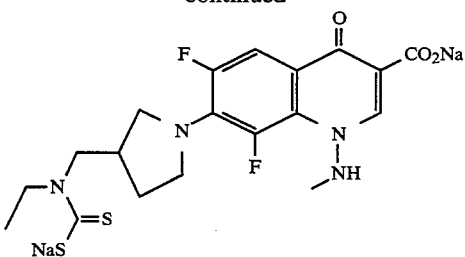
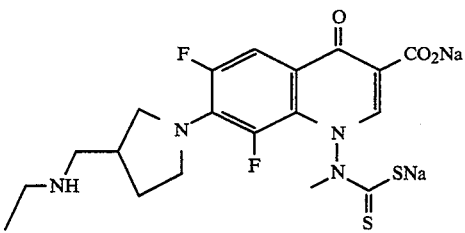
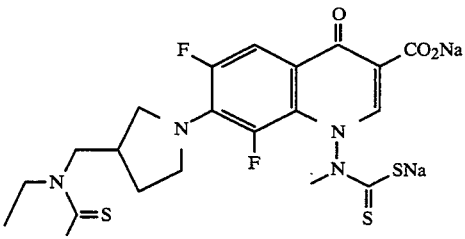
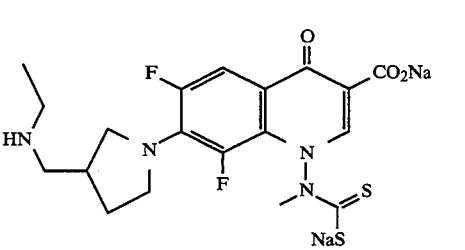
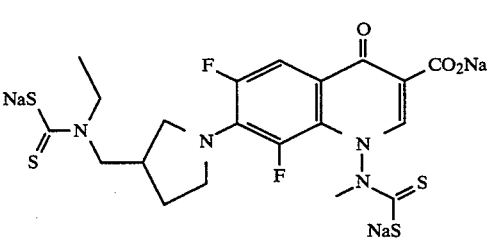
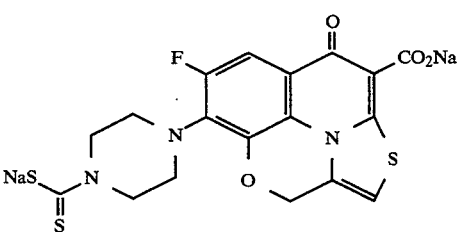
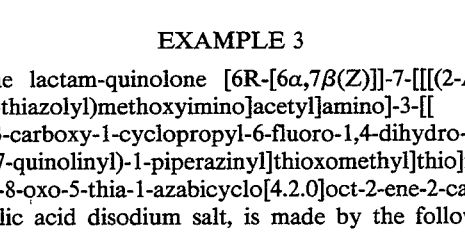
EXAMPLE 3
The lactam-quinolone [6R-[6α,7β(Z)]]-7-[[[(2-Amino-4-thiazolyl)methoxyimino]acetyl]amino]-3-[[ [[4-(3-carboxy-1-cyclopropyl-6-fluoro-1,4-dihydro-4-oxo-7-quinolinyl)-1-piperazinyl]thioxomethyl]thio]methyl]-8-oxo-5-thia-1-azabicyclo[4.2.0]oct-2-ene-2-carboxylic acid disodium salt, is made by the following general reaction sequence, using a compound of this invention as an intermediate.

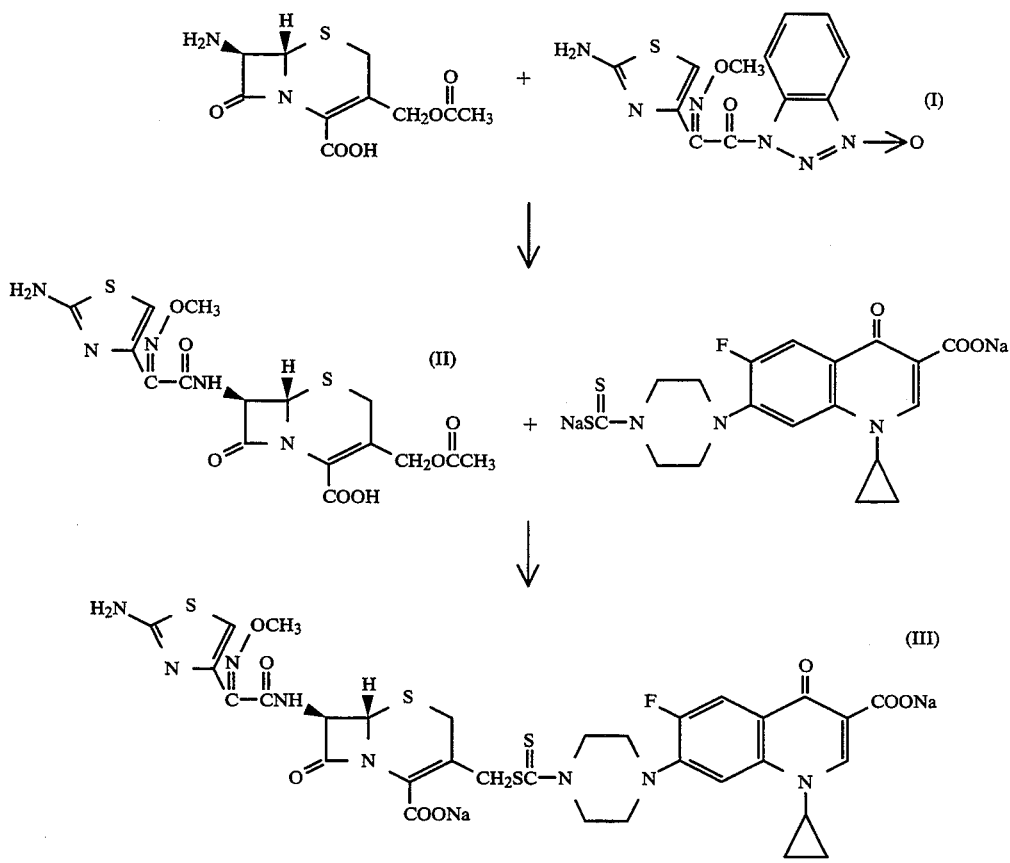

Approximately 11.4 g of 1-hydroxybenzotriazole hydrate is dissolved in approximately 90 ml of N,N-dimethylacetamide (DMAC). Approximately 12.6 ml of triethylamine is added and the solution cooled in an ice/acetone bath. Approximately 6.3 ml of methanesulfonyl chloride 1.09 in DMAC is added dropwise at approximately 0° C. (32° F.) over approximately 25 minutes. The reaction is stirred for an additional 90 minutes. Approximately 15 g of 2-amino-2-(methoxyimino)-4-thiazoleacetic acid is then added. After the addition is complete, approximately 11.3 ml of triethylamine is added dropwise, at approximately 5° C. (41° F.) over approximately 30 minutes. The reaction is then stirred for an additional 105 minutes. Water is added dropwise over 20 minutes and the temperature increased to approximately 20° C. (68° F.). The suspension is stirred for 10 minutes, then a precipitate collected by filtration, washed with large volumes of water, and dried to yield product (I).

Approximately 8 g of 7-aminocephalosporanic acid is suspended in 50% aqueous acetone and cooled in an ice bath. Approximately 3.7 ml of triethylamine is added slowly. Approximately 11 g of product (I) is added, at approximately 2° C. (35° F.). Solutions of saturated aqueous potassium phosphate monobasic (pH 4.5) and 45% aqueous potassium phosphate dibasic (pH 10) are added as necessary to maintain a pH of approximately 7.5. After the addition of product (I) is complete, the mixture is stirred at approximately 2° C. (35° F.) approximately 2 hours, and stirred at room temperature for approximately 3 hours. The acetone is removed by evaporation and the aqueous solution cooled in ice. The solution is then layered with ethyl acetate and adjusted to approximately pH 2.3 with concentrated hydrochloric acid. The layers are separated and the aqueous phase extracted with ethyl acetate. The organic extracts are combined and evaporated. The residue is stirred in ether and collected by filtration yielding product (II).

Approximately 1.5 g of product (II) is suspended in water (24 ml), and approximately 0.27 g of sodium bicarbonate is added, followed by approximately 1.2 g of product (I) from Example II. The solution is stirred at approximately 42° C. (107° F.) for 24 hours. The solvent is removed under vacuum, and the residue is stirred in acetone for 20 minutes and collected by filtration, yielding the final product (III).

EXAMPLE 4

An antimicrobial composition for parenteral administration, according to this invention, is made comprising:

| Component | Amount |
|---|---|
| 1-Cyclopropyl-6-fluoro-1,4-dihydro-7-[4-(mercapto)thioxomethyl]-1-piperazinyl]-4-oxo-3-quinoline carboxylic acid, Disodium Salt[1] | 100 mg/ml carrier |
| Carrier: sodium citrate buffer with (percent by weight of carrier): | |
| lecithin | 0.48% |
| carboxymethylcellulose | 0.53 |
| povidone | 0.50 |
| methyl paraben | 0.11 |

-continued

| Component | Amount |
|---|---|
| propyl paraben | 0.011 |

[1]: a dithiocarbamoyl quinolone, made according to Example 1

The above ingredients are mixed, forming a suspension. Approximately 2.0 ml of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated.

EXAMPLE 5

An enteric coated antimicrobial composition for oral administration, according to this invention, is made comprising the following core tablet:

| Component | Amount (mg) |
|---|---|
| 1-Cyclopropyl-6-fluoro-1,4-dihydro-7-[4-(mercapto)thioxomethyl]-1-piperazinyl]-4-oxo-3-quinoline carboxylic acid, Disodium Salt[1] | 350.0 |
| starch | 30.0 |
| magnesium stearate | 5.0 |
| microcrystalline cellulose | 100.0 |
| colloidal silicon dioxide | 2.5 |
| povidone | 12.5 |

[1]: a dithiocarbamoyl quinolone, made according to Example 1

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 14 days. Symptoms of the disease then subside, indicating substantial eradication of the pathogen.

What is claimed is:

1. A dithiocarbamate-containing compound having one of the following structures:

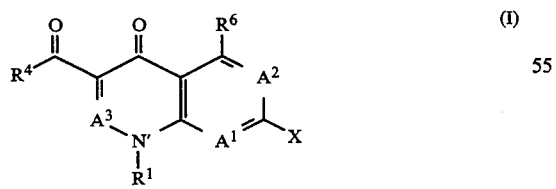

(I)

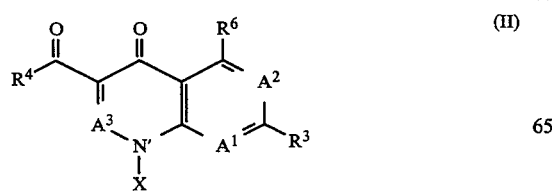

(II)

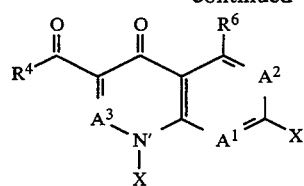

(III)

wherein
(A)
  (1) X is the dithiocarbamate-containing moiety
  $—R^{15}—N(R^{16})(R^{17})$ or $—R^{15}—R^{18}—N(R^{19})(R^{17})$, where
  (a)
    (1) $R^{15}$ is nil; $C_1-C_8$ alkyl; a 3–9 atom monocyclic or 7–17 atom polycyclic carbocycle; or a 4–9 atom monocyclic or 7–17 atom polycyclic heterocycle; wherein said heterocycles have one or more heteroatoms chosen from O, S, or N; and
    (2) $R^{16}$ is hydrogen; $C_1-C_8$ alkyl; $C_2-C_8$ alkenyl; a 3–9 atom monocyclic or 7–17 atom polycyclic carbocycle; a 4–9 atom monocyclic or 7–17 atom polycyclic heterocycle; wherein said heterocycles have one or more heteroatoms chosen from O, S, or N; or
    (3) when X is $R^{15}—N(R^{16})(R^{17})$, $R^{16}$ and $R^{15}$ may together comprise a 4–9 atom monocyclic or 7–17 atom polycyclic heterocycle including the nitrogen atom to which $R^{15}$ and $R^{16}$ are bonded; wherein said heterocycles have one or more heteroatoms chosen from O, S, or N;
  (b) $R^{17}$ is $—C(=S)—S—M$, where M is a pharmaceutically-acceptable salt or biohydrolyzable ester; and
  (c) (1) $R^{18}$ is $C_1-C_8$ alkyl; a 3–9 atom monocyclic or 7–17 atom polycyclic carbocycle; or a 4–9 atom monocyclic or 7–17 atom polycyclic heterocycle; wherein said heterocycles have one or more heteroatoms chosen from O, S, or N; and
    (2) $R^{19}$ is hydrogen; $C_1-C_8$ alkyl; $C_2-C_8$ alkenyl; a 3–9 atom monocyclic or 7–17 atom polycyclic carbocycle; or a 4–9 atom monocyclic or 7–17 atom polycyclic heterocycle; wherein said heterocycles have one or more heteroatoms chosen from O, S, or N; or
    (3) $R^{18}$ and $R^{19}$ may together comprise a 4–9 atom monocyclic or 7–17 atom polycyclic heterocycle including the nitrogen atom to which $R^{18}$ and $R^{19}$ are bonded; wherein said heterocycles have one or more heteroatoms chosen from O, S, or N;
(2) $A^1$ is $C(R^7)$; where
  (i) $R^7$ is hydrogen, hydroxy, alkoxy, nitro, cyano, halogen, $C_1-C_8$ alkyl, or $N(R^8)(R^9)$, and
  (ii) $R^8$ and $R^9$ are, independently, $R^{8a}$; where $R^{8a}$ is hydrogen; $C_1-C_8$ alkyl; $C_2-C_8$ alkenyl; a 3–9 atom monocyclic or 7–17 atom polycyclic carbocycle; or a 4–9 atom monocyclic or 7–17 atom polycyclic heterocycle; or $R^8$ and $R^9$ together comprise a 4–9 atom monocyclic or 7–17 atom polycyclic heterocycle that includes the nitrogen atom to which they are bonded; wherein said heterocycles have one or more heteroatoms chosen from O, S, or N;
(3) $A^2$ is $C(R^2)$; where $R^2$ is hydrogen or halogen;
(4) $A^3$ is $C(R^5)$; where $R^5$ is hydrogen;
(5) $R^1$ is hydrogen; $C_1$-$C_8$ alkyl; a 3-9 atom monocyclic or 7-17 atom polycyclic carbocycle; a 4-9 atom monocyclic or 7-17 atom polycyclic heterocycle; alkoxy; hydroxy; $C_2$-$C_8$ alkenyl; arylalkyl; or $N(R^8)(R^9)$; wherein said heterocycles have one or more heteroatoms chosen from O, S, or N;
(6) $R^3$ is hydrogen; halogen; $C_1$-$C_8$ alkyl; a 3-9 atom monocyclic or 7-17 atom polycyclic carbocycle; or a 4-9 atom monocyclic or 7-17 atom polycyclic heterocycle; wherein said heterocycles have one or more heteroatoms chosen from O, S, or N;
(7) $R^4$ is hydroxy; and
(8) $R^6$ is hydrogen, halogen, nitro or $N(R^8)(R^9)$;

(B) and where
(1) $R^1$ and $R^7$ may together comprise a 4-9 atom monocyclic or 7-17 atom polycyclic heterocycle including N' and $A^1$; wherein said heterocycles have one or more heteroatoms chosen from O, S, or N;
(2) $R^2$ and $R^3$ may together comprise —O—$(CH_2)_n$—O—, where n is from 1 to 4;
(3) $R^4$ and $R^5$ may together comprise a 4-9 atom monocyclic or 7-17 atom polycyclic heterocycle including the carbon atoms to which $R^4$ and $R^5$ are bonded and the carbon atom to which said carbon atoms are bonded; wherein said heterocycles have one or more heteroatoms chosen from O, S, or N; and
(4) $R^1$ and $R^5$ may together comprise a 4-9 atom monocyclic or 7-17 atom polycyclic heterocycle including N' and the adjacent carbon to which $R^5$ is bonded; wherein said heterocycles have one or more heteroatoms chosen from O, S, or N;

and pharmaceutically-acceptable salts and biohydrolyzable esters thereof, and hydrates thereof.

2. A compound according to claim 1, wherein when one or more of $R^{15}$, $R^{16}$, $R^{18}$, or $R^{19}$ is a monocyclic carbocycle, said monocyclic carbocycle has from 4-9 atoms.

3. A dithiocarbamate-containing compound having one of the following structures:

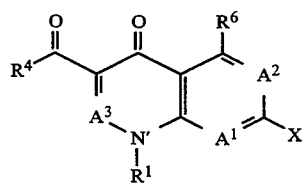   (I)

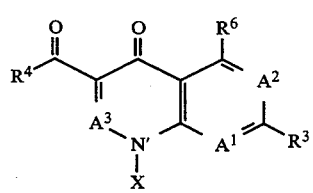   (II)

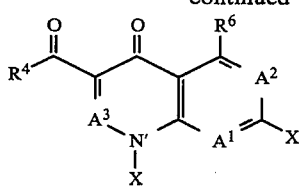   (III)

wherein
(A)
(1) X is the dithiocarbamate-containing moiety —$R^{15}$—$N(R^{16})(R^{17})$ or —$R^{15}$—$R^{18}$—$N(R^{19})(R^{17})$, where
(a)
(1) $R^{15}$ is nil; $C_1$-$C_8$ alkyl; a 3-9 atom monocyclic or 7-17 atom polycyclic carbocycle; or a 4-9 atom monocyclic or 7-17 atom polycyclic heterocycle; wherein said heterocycles have one or more heteroatoms chosen from O, S, or N; and
(2) $R^{16}$ is hydrogen; $C_1$-$C_8$ alkyl; $C_2$-$C_8$ alkenyl; a 3-9 atom monocyclic or 7-17 atom polycyclic carbocycle; or a 4-9 atom monocyclic or 7-17 atom polycyclic heterocycle; wherein said heterocycles have one or more heteroatoms chosen from O, S, or N; or
(3) when X is $R^{15}$—$N(R^{16})(R^{17})$, $R^{16}$ and $R^{15}$ may together comprise a 4-9 atom monocyclic or 7-17 atom polycyclic heterocycle including the nitrogen atom to which $R^{15}$ and $R^{16}$ are bonded; wherein said heterocycles have one or more heteroatoms chosen from O, S, or N;
(b) $R^{17}$ is —C(=S)—S—M, where M is a pharmaceutically-acceptable salt or biohydrolyzable ester; and
(c)
(1) $R^{18}$ is $C_1$-$C_8$ alkyl; a 3-9 atom monocyclic or 7-17 atom polycyclic carbocycle; or a 4-9 atom monocyclic or 7-17 atom polycyclic heterocycle; wherein said heterocycles have one or more heteroatoms chosen from O, S, or N; and
(2) $R^{19}$ is hydrogen; $C_1$-$C_8$ alkyl; $C_2$-$C_8$ alkenyl; a 3-9 atom monocyclic or 7-17 atom polycyclic carbocycle; or a 4-9 atom monocyclic or 7-17 atom polycyclic heterocycle; wherein said heterocycles have one or more heteroatoms chosen from O, S, or N; or
(3) $R^{18}$ and $R^{19}$ may together comprise a 4-9 atom monocyclic or 7-17 atom polycyclic heterocycle including the nitrogen atom to which $R^{18}$ and $R^{19}$ are bonded; wherein said heterocycles have one or more heteroatoms chosen from O, S, or N;
(2) $A^1$ is $C(R^7)$; where $R^7$ is hydrogen or halogen,
(3) $A^2$ is $C(R^2)$; where $R^2$ is halogen;
(4) $A^3$ is $C(R^5)$; where $R^5$ is hydrogen;
(5) $R^1$ is $C_1$-$C_8$ alkyl or a 3-9 atom monocyclic or 7-17 atom polycyclic carbocycle;
(6) $R^3$ is a 4-9 atom monocyclic or 7-17 atom polycyclic heterocycle; wherein said heterocycles have one or more heteroatoms chosen from O, S, or N;
(7) $R^4$ is hydroxy; and
(8) $R^6$ is hydrogen;

(B) and where
(1) $R^1$ and $R^7$ may together comprise a 4–9 atom monocyclic or 7–17 atom polycyclic heterocycle including N' and $A^1$; wherein said heterocycles have one or more heteroatoms chosen from O, S, or N;
(2) $R^2$ and $R^3$ may together comprise —O—(CH$_2$)$_n$—O—, where n is from 1 to 4;
(3) $R^4$ and $R^5$ may together comprise a 4–9 atom monocyclic or 7–17 atom polycyclic heterocycle including the carbon atoms to which $R^4$ and $R^5$ are bonded and the carbon atom to which said carbon atoms are bonded; wherein said heterocycles have one or more heteroatoms chosen from O, S, or N; and
(4) $R^1$ and $R^5$ may together comprise a 4–9 atom monocyclic or 7–17 atom polycyclic heterocycle including N' and the adjacent carbon to which $R^5$ is bonded; wherein said heterocycles have one or more heteroatoms chosen from O, S, or N;

and pharmaceutically-acceptable salts and biohydrolyzable esters thereof, and hydrates thereof.

4. A compound according to claim 3, wherein when one or more of $R^{15}$, $R^{16}$, $R^{18}$, or $R^{19}$ is a monocyclic carbocycle, said monocyclic carbocycle has from 4–9 atoms.

5. A dithiocarbamate-containing compounds having the following structure:

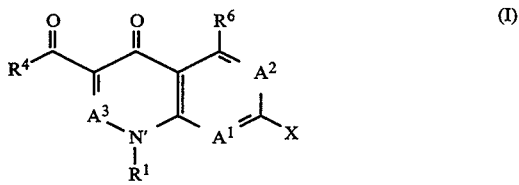

wherein
(A)
(1) X is the dithiocarbamate-containing moiety —$R^{15}$—N($R^{16}$)($R^{17}$) or —$R^{15}$—$R^{18}$—N($R^{19}$)($R^{17}$), where
(a)
(1) $R^{15}$ is nil; C$_1$–C$_8$ alkyl; a 3–9 atom monocyclic or 7–17 atom polycyclic carbocycle; or a 4–9 atom monocyclic or 7–17 atom polycyclic heterocycle; wherein said heterocycles have one or more heteroatoms chosen from O, S, or N; and
(2) $R^{16}$ is hydrogen; C$_1$–C$_8$ alkyl; C$_2$–C$_8$ alkenyl; a 3–9 atom monocyclic or 7–17 atom polycyclic carbocycle; or a 4–9 atom monocyclic or 7–17 atom polycyclic heterocycle; wherein said heterocycles have one or more heteroatoms chosen from O, S, or N; or
(3) when X is $R^{15}$—N($R^{16}$)($R^{17}$), $R^{16}$ and $R^{15}$ may together comprise a 4–9 atom monocyclic or 7–17 atom polycyclic heterocycle including the nitrogen atom to which $R^{15}$ and $R^{16}$ are bonded; wherein said heterocycles have one or more heteroatoms chosen from O, S, or N;
(b) $R^{17}$ is —C(=S)—S—M, where M is a pharmaceutically-acceptable salt or biohydrolyzable ester; and
(c)

(1) $R^{18}$ is C$_1$–C$_8$ alkyl; a 3–9 atom monocyclic or 7–17 atom polycyclic carbocycle; or a 4–9 atom monocyclic or 7–17 atom polycyclic hetero cycle; wherein said heterocycles have one or more heteroatoms chosen from O, S, or N; and
(2) $R^{19}$ is hydrogen; C$_1$–C$_8$ alkyl; C$_2$–C$_8$ alkenyl; a 3–9 atom monocyclic or 7–17 atom polycyclic carbocycle; or a 4–9 atom monocyclic or 7–17 atom polycyclic heterocycle; wherein said heterocycles have one or more heteroatoms chosen from O, S, or N; or
(3) $R^{18}$ and $R^{19}$ may together comprise a 4–9 atom monocyclic or 7–17 atom polycyclic heterocycle including the nitrogen atom to which $R^{18}$ and $R^{19}$ are bonded; wherein said heterocycles have one or more heteroatoms chosen from O, S, or N;
(2) $A^1$ is C($R^7$); where $R^7$ is hydrogen or halogen;
(3) $A^2$ is C($R^2$); where $R^2$ is hydrogen or halogen;
(4) $A^3$ is C($R^5$); where $R^5$ is hydrogen;
(5) $R^1$ is C$_1$–C$_8$ alkyl; aryl; cycloalkyl; or alkylamino;
(6) $R^4$ is hydroxy; and
(7) $R^6$ is hydrogen, halogen, nitro or N($R^8$)($R^9$);

(B) and where $R^4$ and $R^5$ may together comprise a 4–9 atom monocyclic or 7–17 atom polycyclic heterocycle including the carbon atoms to which $R^4$ and $R^5$ are bonded and the carbon atom to which said carbon atoms are bonded; wherein said heterocycles have one or more heteroatoms chosen from O, S, or N;

and pharmaceutically-acceptable salts and biohydrolyzable esters thereof, and hydrates thereof.

6. A compound according to claim 5, wherein when one or more of $R^{15}$, $R^{16}$, $R^{18}$, or $R^{19}$ is a monocyclic carbocycle, said monocyclic carbocycle has from 4–9 atoms.

7. A compound, according to claim 4, wherein $R^1$ is C$_1$–C$_8$ alkyl, aryl, cycloalkyl, or alkylamino.

8. A compound, according to claim 7, wherein $R^1$ is ethyl, 2-fluoroethyl, 2-hydroxyethyl, t-butyl, 4-fluorophenyl, 2,4-difluorophenyl, methylamino or cyclopropyl.

9. A compound, according to claim 7, wherein $R^7$ is hydrogen or halogen.

10. A compound, according to claim 9, wherein $R^7$ is chlorine or fluorine.

11. A compound, according to claim 5, wherein X is —$R^{15}$—N($R^{16}$)($R^{17}$).

12. A compound, according to claim 11, wherein $R^{16}$ is hydrogen and $R^{15}$ is a 4–9 atom monocyclic or a 7–17 atom polycyclic heterocycle having one or more heteroatoms selected from O, S, or N.

13. A compound, according to claim 12, wherein said heterocyclic ring is pyrrolidine.

14. A compound, according to claim 13, wherein $R^1$ is cyclopropyl, and $R^2$ is fluorine.

15. A compound, according to claim 14, wherein X is 3-[[mercapto(thioxomethyl)]amino]pyrrolidine.

16. A compound according to claim 11, wherein $R^{16}$ and $R^{15}$ together comprise a 4–9 atom monocyclic or a 7–17 atom polycyclic heterocycle having one or more heteroatoms selected from O, S, or N including the nitrogen atom to which $R^{15}$ and $R^{16}$ are bonded.

17. A compound, according to claim 16, wherein $R^1$ is cyclopropyl, and $R^2$ is fluorine.

18. A compound, according to claim 17, wherein said heterocyclic ring is is piperazine, 3-methylpiperazine, or 3,5 -dimethylpiperazine.

19. A compound, according to claim 18, wherein said heterocyclic ring is piperazine.

20. A compound, according to claim 5, wherein X is $-R^{15}-R^{18}-N(R^{19})(R^{17})$.

21. A compound according to claim 20, wherein $R^{18}$ is a $C_1$–$C_8$ alkyl and $R^{15}$ is a 4–9 atom monocyclic or a 7–17 atom polycyclic heterocycle having one or more heteroatoms selected from O, S, or N.

22. A compound, according to claim 21, wherein $R^1$ is cyclopropyl, and $R^2$ is fluorine.

23. A compound, according to claim 22, wherein said heterocyclic ring is is 3-aminomethylpyrrolidine, N-methylaminomethylpyrrolidine, or N-ethylaminomethylpyrrolidine.

24. A composition for treating or preventing an infectious disorder in a human or other animal subject, comprising:
  (1) a safe and effective amount of a compound of claim 1; and
  (2) a pharmaceutically-acceptable carrier.

25. A composition for treating or preventing an infectious disorder in a human or other animal subject, comprising:
  (1) a safe and effective amount of a compound of claim 5; and
  (2) a pharmaceutically-acceptable carrier.

26. A composition for treating or preventing an infectious disorder in a human or other animal subject, comprising:
  (1) a safe and effective amount of a compound of claim 15; and
  (2) a pharmaceutically-acceptable carrier.

27. A composition for treating or preventing an infectious disorder in a human or other animal subject, comprising:
  (1) a safe and effective amount of a compound of claim 18; and
  (2) a pharmaceutically-acceptable carrier.

28. A composition for treating or preventing an infectious disorder in a human or other animal subject, comprising:
  (1) a safe and effective amount of a compound of claim 23; and
  (2) a pharmaceutically-acceptable carrier.

29. A composition for treating or preventing an infectious disorder in a human or other animal subject, comprising:
  (1) a safe and effective amount of a compound of claim 3; and
  (2) a pharmaceutically-acceptable carrier.

30. A method for preventing or treating an infectious disorder in a human or other animal subject, by administering to said subject a safe and effective amount of a compound of claim 1.

31. A method for preventing or treating an infectious disorder in a human or other animal subject, by administering to said subject a safe and effective amount of a compound of claim 5.

32. A method for preventing or treating an infectious disorder in a human or other animal subject, by administering to said subject a safe and effective amount of a compound of claim 15.

33. A method for preventing or treating an infectious disorder in a human or other animal subject, by administering to said subject a safe and effective amount of a compound of claim 18.

34. A method for preventing or treating an infectious disorder in a human or other animal subject, by administering to said subject a safe and effective amount of a compound of claim 23.

35. A method for preventing or treating an infectious disorder in a human or other animal subject, by administering to said subject a safe and effective amount of a compound of claim 3.

* * * * *